(12) United States Patent
Salam et al.

(10) Patent No.: US 11,993,877 B2
(45) Date of Patent: May 28, 2024

(54) LATEX-FREE AND FORMALDEHYDE-FREE NONWOVEN FABRICS

(71) Applicant: Glatfelter Corporation, Charlotte, NC (US)

(72) Inventors: Abdus Salam, Harrisburg, NC (US); Timothy Kistemaker, Mooresville, NC (US)

(73) Assignee: Glatfelter Corporation, Charlotte, NC (US)

( * ) Notice: Subject to any disclaimer, the term of this patent is extended or adjusted under 35 U.S.C. 154(b) by 82 days.

(21) Appl. No.: 17/280,778

(22) PCT Filed: Jan. 31, 2019

(86) PCT No.: PCT/US2019/016041
§ 371 (c)(1),
(2) Date: Mar. 26, 2021

(87) PCT Pub. No.: WO2020/068151
PCT Pub. Date: Apr. 2, 2020

(65) Prior Publication Data
US 2022/0002921 A1    Jan. 6, 2022

Related U.S. Application Data

(60) Provisional application No. 62/736,760, filed on Sep. 26, 2018.

(51) Int. Cl.
*D04H 1/425* (2012.01)
*D04H 1/587* (2012.01)
*D04H 1/593* (2012.01)

(52) U.S. Cl.
CPC ............. *D04H 1/425* (2013.01); *D04H 1/587* (2013.01); *D04H 1/593* (2013.01)

(58) Field of Classification Search
CPC .......... D04H 1/425; D04H 1/587; D04H 1/64; D04H 1/641; C08L 1/286; C08L 2201/06;
(Continued)

(56) References Cited

U.S. PATENT DOCUMENTS

| 206,632 A | 7/1878 | Snell |
| 797,749 A | 8/1905 | Robinson et al. |

(Continued)

FOREIGN PATENT DOCUMENTS

| EP | 2309059 A1 * | 4/2011 | ......... C09D 101/286 |
| EP | 2309059 A1 | 4/2011 | |

(Continued)

OTHER PUBLICATIONS

International Preliminary Report on Patentability received for PCT Application No. PCT/US2019/016041, mailed on Apr. 8, 2021, 12 Pages.

(Continued)

*Primary Examiner* — Jeremy R Pierce
*Assistant Examiner* — Christine X Nisula
(74) *Attorney, Agent, or Firm* — Blank Rome LLP

(57) ABSTRACT

A nonwoven fabric comprising a fiber web in an amount of 85-99.99 wt. %, and a cured natural binder in an amount of 0.01-15 wt. %; wherein the fiber web comprises natural fibers and synthetic fibers; wherein natural fibers are present in the nonwoven fabric in an amount of 70-90 wt. %; wherein synthetic fibers are present in the nonwoven fabric in an amount of from 10-30 wt. %; wherein the cured natural binder comprises modified cellulose and a strengthening agent in a weight ratio of strengthening agent to modified cellulose of 1:2 to 1:1,000, wherein modified cellulose comprises CMC and/or sodium CMC, wherein the strengthening agent comprises a crosslinking agent and/or a wet strength agent, wherein the crosslinking agent comprises a (Continued)

Pulp and Bico Fiber Ratio (g/m²) at Each Layer

Latex-Free MBAL Product (50 gsm)

Regular MBAL Product (58 gsm)

carboxylic acid having two or more carboxyl groups, and wherein the wet strength agent comprises a reactive functional group selected from the group consisting of halide, chloride, fluoride, hydroxyl, and combinations thereof.

14 Claims, 3 Drawing Sheets

(58) Field of Classification Search
CPC ....... D06M 15/09; D21H 21/18; D21H 21/20; D21H 17/25
See application file for complete search history.

(56) References Cited

U.S. PATENT DOCUMENTS

| | | |
|---|---|---|
| 874,418 A | 12/1907 | McEvoy |
| 2,543,870 A | 3/1951 | Robbins |
| 2,588,533 A | 3/1952 | Victor |
| 2,861,319 A | 11/1958 | Breen |
| 2,931,091 A | 4/1960 | Breen |
| 2,989,798 A | 6/1961 | Bannerman |
| 3,038,235 A | 6/1962 | Joseph |
| 3,081,490 A | 3/1963 | Wilhelm et al. |
| 3,117,362 A | 1/1964 | Leonard |
| 3,121,254 A | 2/1964 | Wilhelm et al. |
| 3,163,170 A | 12/1964 | Gates |
| 3,188,689 A | 6/1965 | Leonard |
| 3,237,245 A | 3/1966 | Kunijiro et al. |
| 3,249,669 A | 5/1966 | Jamieson |
| 3,301,746 A | 1/1967 | Sanford |
| 3,457,342 A | 7/1969 | Parr et al. |
| 3,466,703 A | 9/1969 | Heckrotte |
| 3,469,279 A | 9/1969 | Hudgell |
| 3,500,498 A | 3/1970 | Fukuma et al. |
| 3,585,685 A | 6/1971 | Mcdermott |
| 3,692,423 A | 9/1972 | Okamoto et al. |
| 3,716,317 A | 2/1973 | Williams et al. |
| 3,778,208 A | 12/1973 | Bisset et al. |
| 3,787,162 A | 1/1974 | Cheetham |
| 3,814,561 A | 6/1974 | Matsui et al. |
| 3,931,386 A | 1/1976 | Kimura et al. |
| 3,963,406 A | 6/1976 | Reker |
| 3,992,499 A | 11/1976 | Lee |
| 4,014,635 A | 3/1977 | Kroyer |
| 4,021,410 A | 5/1977 | Koyama et al. |
| 4,052,146 A | 10/1977 | Sternberg |
| 4,115,989 A | 9/1978 | Spolnicki |
| 4,217,321 A | 8/1980 | Campbell |
| 4,237,187 A | 12/1980 | Raybon, Jr. et al. |
| 4,251,200 A | 2/1981 | Parkin |
| 4,264,289 A | 4/1981 | Day |
| 4,335,066 A | 6/1982 | Dinius |
| 4,350,006 A | 9/1982 | Okamoto et al. |
| 4,351,793 A | 9/1982 | Day |
| 4,366,111 A | 12/1982 | Dinius et al. |
| 4,370,114 A | 1/1983 | Okamoto et al. |
| 4,375,447 A | 3/1983 | Chung |
| 4,375,448 A | 3/1983 | Appel et al. |
| 4,406,850 A | 9/1983 | Hills |
| 4,434,204 A | 2/1984 | Hartman et al. |
| 4,445,833 A | 5/1984 | Moriki et al. |
| 4,529,368 A | 7/1985 | Makansi |
| 4,582,666 A | 4/1986 | Kenworthy et al. |
| 4,609,710 A | 9/1986 | Iohara et al. |
| 4,640,810 A | 2/1987 | Laursen |
| 4,666,390 A | 5/1987 | Kenworthy et al. |
| 4,687,610 A | 8/1987 | Vassilatos |
| 4,717,325 A | 1/1988 | Fujimura et al. |
| 4,732,552 A | 3/1988 | Chung |
| 4,743,189 A | 5/1988 | Samuelson |
| 4,950,541 A | 8/1990 | Tabor et al. |
| 5,076,774 A | 12/1991 | Farrington et al. |
| 5,082,899 A | 1/1992 | Sawyer et al. |
| 5,126,199 A | 6/1992 | Sawyer et al. |
| 5,162,074 A | 11/1992 | Hills |
| 5,185,199 A | 2/1993 | Sawyer et al. |
| 5,229,060 A | 7/1993 | Knox et al. |
| 5,234,550 A | 8/1993 | Ekholm et al. |
| 5,256,050 A | 10/1993 | Davies |
| 5,336,709 A | 8/1994 | Antikow et al. |
| 5,372,885 A | 12/1994 | Tabor et al. |
| 5,456,982 A | 10/1995 | Hansen et al. |
| 5,492,759 A | 2/1996 | Eriksson et al. |
| 5,505,889 A | 4/1996 | Davies |
| 5,566,611 A | 10/1996 | Scheucher et al. |
| 5,582,913 A | 12/1996 | Simons |
| 5,601,921 A | 2/1997 | Eriksson |
| 5,634,249 A | 6/1997 | Ballarati |
| 5,660,804 A | 8/1997 | Ochi et al. |
| 5,705,565 A | 1/1998 | Hughes et al. |
| 5,773,825 A | 6/1998 | Doyle |
| 5,811,186 A | 9/1998 | Martin et al. |
| 5,849,232 A | 12/1998 | Ochi et al. |
| 5,905,046 A * | 5/1999 | Takeda .................. D04H 1/587 428/913 |
| 5,972,463 A | 10/1999 | Martin et al. |
| 6,080,482 A | 6/2000 | Martin et al. |
| 6,159,335 A | 12/2000 | Owens et al. |
| 6,284,145 B1 | 9/2001 | Andersson |
| 6,363,580 B1 | 4/2002 | Soerensen et al. |
| 6,670,035 B2 | 12/2003 | Pittman et al. |
| 6,726,461 B2 | 4/2004 | Hyvarinen et al. |
| 6,841,245 B2 | 1/2005 | Chang et al. |
| 6,855,422 B2 | 2/2005 | Magill et al. |
| 2009/0308551 A1* | 12/2009 | Kokko .................. D21H 17/45 162/146 |
| 2018/0001591 A1 | 1/2018 | Dutkiewicz et al. |
| 2019/0284368 A1* | 9/2019 | Aydin ..................... B05D 5/08 |
| 2019/0299499 A1* | 10/2019 | Pedersen ................ B29C 65/02 |

FOREIGN PATENT DOCUMENTS

| | | |
|---|---|---|
| JP | H07119010 A | 5/1995 |
| JP | H0733988 U | 6/1995 |
| KR | 20110136174 A | 12/2011 |
| WO | 2009151612 A2 | 12/2009 |
| WO | 2020068151 A1 | 4/2020 |

OTHER PUBLICATIONS

International Search Report and Written Opinion received for PCT Application No. PCT/US2019/016041, mailed on May 7, 2019, 13 Pages.

U.S. Appl. No. 62/624,377, filed Jan. 31, 2018, 92 Pages.

* cited by examiner

Reaction Mechanism Between Wet Strength Agent and Pulp Fibers

LATEX-FREE AND FORMALDEHYDE-FREE NONWOVEN FABRICS

CROSS REFERENCE TO RELATED APPLICATIONS

This application is a national phase entry of International Application No. PCT/US2019/016041, filed on Jan. 31, 2019, which claims the benefit of priority to U.S. Provisional Application No. 62/736,760 filed on Sep. 26, 2018, the contents of which are hereby incorporated by reference in their entirety.

TECHNICAL FIELD

The present disclosure relates to binder compositions for nonwovens, more specifically latex-free and formaldehyde-free nonwoven materials and methods of making and using same.

BACKGROUND

Nonwovens are generally used in a wide range of consumer and industrial products with diverse properties, including healthcare and surgical fabrics, wipes, absorbent hygiene products, apparel, home furnishings, construction, filtration and engineering. A nonwoven material is a sheet of fibers, continuous filaments (e.g., fiber precursors), or chopped yarns of any nature or origin, that have been formed into a web by any means, and bonded together by any means, with the exception of weaving or knitting.

Some nonwoven fabrics have sufficient web strength after forming to be handled even if they are subsequently additionally bonded, for example when a bonding step is an integral part of the web-forming process, as in spun-bond and melt-blown nonwovens. Most other webs have relatively little strength as formed and may require an additional bonding step (e.g., chemical bonding) in order to make the nonwoven web suitable for its intended end use.

Chemical bonding in nonwoven products normally refers to the use of latex binders, which have been in existence at least as long as most modern nonwovens themselves. A benefit of latex binders is their overall versatility and utility. However, latex binders are expensive and require the use of large volumes of binder to achieve the minimum target quality. Further, latex binders can raise environmental and health concerns pertaining to non-biodegradability, volatile organic compound emissions and formaldehyde formation. Another issue during nonwoven fabric manufacturing is a high dust level, which can be difficult to control with latex binders, potentially posing health, safety and environmental concerns.

Thermal-bonded airlaid (TBAL) nonwovens are generally produced without a binder, and thus contain only wood pulp and relatively high amounts of bicomponent fiber (e.g., 31 wt. %), which causes the production cost of the raw materials to be significantly higher than the production cost of multi-bonded airlaid (MBAL) nonwovens. Generally, MBAL nonwovens can be produced with pulp fiber, bicomponent fiber (e.g., 20 wt. %) and latex binder (e.g., 6 wt. %). However, MBAL nonwovens require a relatively high basis weight to display the same desired physical properties as TBAL nonwovens. Further, conventional MBAL nonwovens use latex binders, which can raise environmental and health concerns. While TBAL and MBAL nonwovens refer to (e.g., represent) multi-layer nonwoven fabrics, single-layer chemically-bonded nonwoven fabrics can also contain latex (e.g., latex-bonded airlaid (LBAL)). Thus, there is an ongoing need for the development of nonwovens (e.g., multi-layer nonwovens, single-layer nonwovens) bonded with binders that are latex-free and formaldehyde-free.

BRIEF SUMMARY

Disclosed herein is a nonwoven fabric comprising a fiber web in an amount of from about 85 wt. % to about 99.99 wt. %, based on the total weight of the nonwoven fabric; and a cured natural binder in an amount of from about 0.01 wt. % to about 15 wt. %, based on the total weight of the nonwoven fabric; wherein the fiber web comprises natural fibers and synthetic fibers; wherein the natural fibers are present in the nonwoven fabric in an amount of from about 70 wt. % to about 90 wt. %, based on the total weight of the nonwoven fabric; wherein the synthetic fibers are present in the nonwoven fabric in an amount of from about 10 wt. % to about 30 wt. %, based on the total weight of the nonwoven fabric; wherein the cured natural binder comprises modified cellulose and a strengthening agent in a weight ratio of strengthening agent to modified cellulose of from about 1:2 to about 1:1,000, wherein the modified cellulose comprises carboxymethylcellulose (CMC) and/or sodium carboxymethylcellulose (sodium CMC), wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof.

Also disclosed herein is a multi-layer nonwoven fabric comprising a fiber web in an amount of from about 85 wt. % to about 99.99 wt. %, based on the total weight of the multi-layer nonwoven fabric; and a cured natural binder in an amount of from about 0.01 wt. % to about 15 wt. %, based on the total weight of the multi-layer nonwoven fabric; wherein the fiber web comprises a first outer layer, a second outer layer, and optionally one or more intermediate layers, wherein the one or more intermediate layers are disposed between the first outer layer and the second outer layer; wherein the first outer layer, the second outer layer, or both the first outer layer and the second outer layer comprise the cured natural binder; wherein each layer of the fiber web comprises natural fibers and synthetic fibers; wherein the cured natural binder comprises modified cellulose and a strengthening agent, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof.

Further disclosed herein is a method of making a nonwoven fabric, the method comprising (a) forming a plurality of fibers into a fiber web; wherein the fiber web comprises natural fibers and synthetic fibers; wherein the natural fibers are present in the fiber web in an amount of from about 70 wt. % to about 90 wt. %, based on the total weight of the fiber web; and wherein the synthetic fibers are present in the fiber web in an amount of from about 10 wt. % to about 30 wt. %, based on the total weight of the fiber web; (b) contacting at least a portion of the fiber web with an aqueous natural binder to form a binder impregnated fiber web, wherein the aqueous natural binder comprises modified cellulose, a strengthening agent, and water, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof; and (c) curing the binder impregnated fiber web to form the nonwoven fabric; wherein the nonwoven fabric comprises the fiber web in an amount of from about 85 wt. % to about 99.99 wt. %, based on the total weight of the nonwoven fabric; and wherein the nonwoven fabric comprises a cured natural binder in an amount of from about 0.01 wt. % to about 15 wt. %, based on the total weight of the nonwoven fabric.

Further disclosed herein is a method of making a multi-layer nonwoven fabric, the method comprising (a) forming a plurality of fibers into a multi-layer fiber web via a dry laid process; wherein the multi-layer fiber web comprises a first outer layer, a second outer layer, and optionally one or more intermediate layers, wherein the one or more intermediate layers are disposed between the first outer layer and the second outer layer; wherein each layer of the multi-layer fiber web comprises natural fibers and synthetic fibers; (b) contacting at least a portion of the first outer layer and/or at least a portion of the second outer layer with an aqueous natural binder to form a binder impregnated fiber web, wherein the aqueous natural binder comprises modified cellulose, a strengthening agent, and water, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof; and (c) curing the binder impregnated fiber web to form the multi-layer nonwoven fabric; wherein the multi-layer nonwoven fabric comprises the multi-layer fiber web in an amount of from about 85 wt. % to about 99.99 wt. %, based on the total weight of the multi-layer nonwoven fabric; and wherein the multi-layer nonwoven fabric comprises a cured natural binder in an amount of from about 0.01 wt. % to about 15 wt. %, based on the total weight of the multi-layer nonwoven fabric.

Further disclosed herein is a multi-layer nonwoven fabric comprising a fiber web in an amount of about 98 wt. %, based on the total weight of the multi-layer nonwoven fabric; and a cured natural binder in an amount of about 2 wt. %, based on the total weight of the multi-layer nonwoven fabric; wherein the fiber web comprises a first outer layer, a second outer layer, and optionally one or more intermediate layers, wherein the one or more intermediate layers are disposed between the first outer layer and the second outer layer; wherein the first outer layer, the second outer layer, or both the first outer layer and the second outer layer comprise the cured natural binder; wherein each layer of the fiber web comprises natural fibers and synthetic fibers; wherein the natural fibers are present in the nonwoven fabric in an amount of about 80 wt. %, based on the total weight of the nonwoven fabric; wherein the synthetic fibers are present in the nonwoven fabric in an amount of about 18 wt. %, based on the total weight of the nonwoven fabric; wherein the cured natural binder comprises modified cellulose and a strengthening agent, wherein the cured natural binder is characterized by a weight ratio of strengthening agent to modified cellulose of from about 1:2 to about 1:1,000, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof.

Further disclosed herein is a single-layer nonwoven fabric comprising a fiber web in an amount of from about 85 wt. % to about 99.99 wt. %, based on the total weight of the single-layer nonwoven fabric; and a cured natural binder in an amount of from about 0.01 wt. % to about 15 wt. %, based on the total weight of the single-layer nonwoven fabric; wherein the fiber web comprises natural fibers; wherein the natural fibers are present in the single-layer nonwoven fabric in an amount of from about 85 wt. % to about 99.99 wt. %, based on the total weight of the single-layer nonwoven fabric; wherein the cured natural binder comprises modified cellulose and a strengthening agent in a weight ratio of strengthening agent to modified cellulose of from about 1:2 to about 1:1,000, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof.

BRIEF DESCRIPTION OF THE DRAWINGS

For a detailed description of the preferred embodiments of the disclosed methods, reference will now be made to the accompanying drawings in which.

DETAILED DESCRIPTION

Figure 1A:
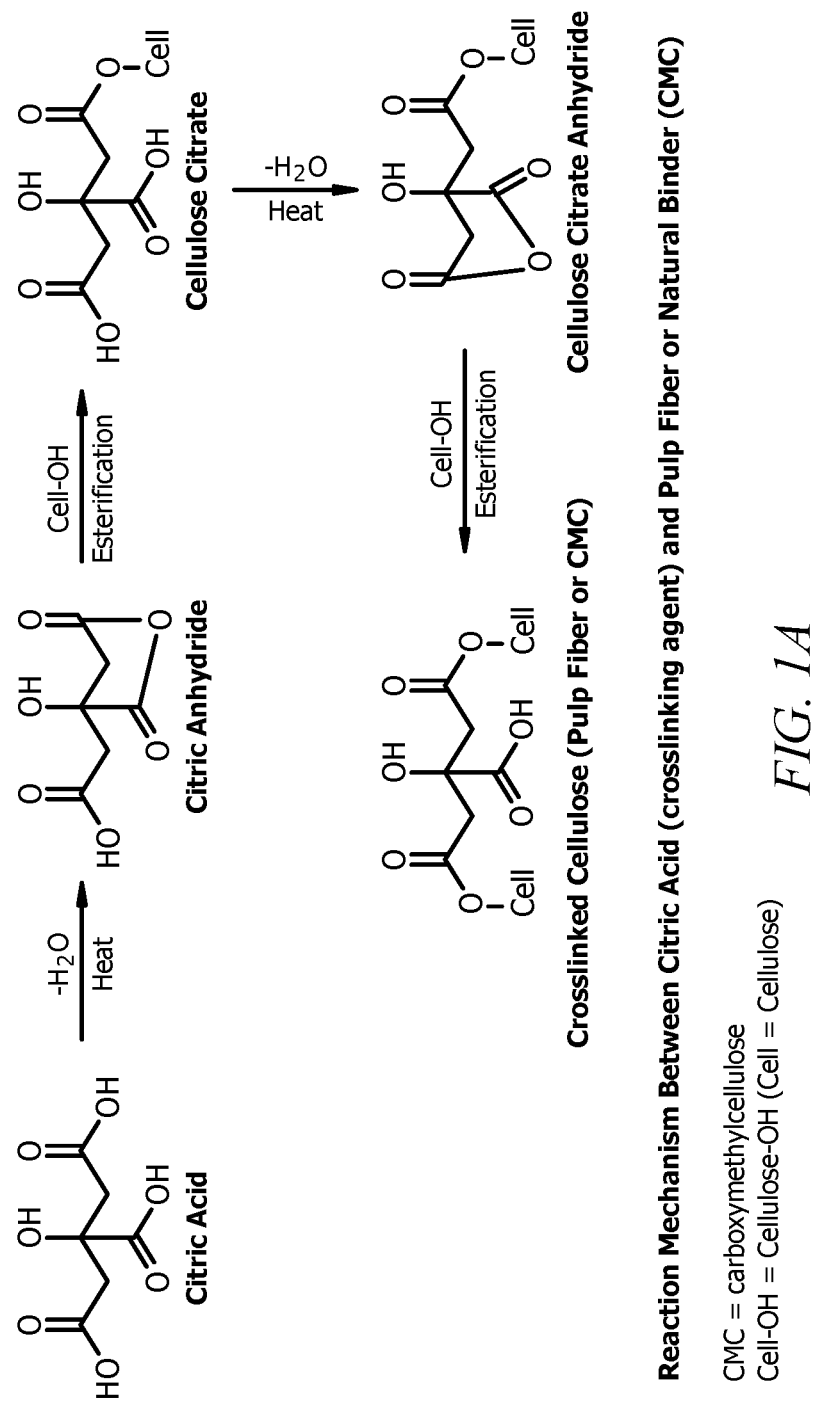
FIGS. 1A and 1B display a proposed reaction mechanism between natural binder containing citric acid or a wet strength agent, respectively, and cellulosic pulp fibers (CMC and/or sodium CMC)

Disclosed herein are nonwoven fabrics and methods of making and using same. In an aspect, a nonwoven fabric can comprise a fiber web in an amount of from about 85 wt. % to about 99.99 wt. %, based on the total weight of the nonwoven fabric; and a cured natural binder in an amount of from about 0.01 wt. % to about 15 wt. %, based on the total weight of the nonwoven fabric; wherein the fiber web comprises natural fibers and synthetic fibers; wherein the natural fibers are present in the nonwoven fabric in an amount of from about 70 wt. % to about 90 wt. %, based on the total weight of the nonwoven fabric; wherein the synthetic fibers are present in the nonwoven fabric in an amount of from about 10 wt. % to about 30 wt. %, based on the total weight of the nonwoven fabric; wherein the cured natural binder comprises modified cellulose and a strengthening agent in a weight ratio of strengthening agent to modified cellulose of from about 1:2 to about 1:1,000, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof. In some aspects, the nonwoven fabric can be a multi-layer nonwoven fabric.

Further disclosed herein is a single-layer nonwoven fabric and methods of making and using same. In an aspect, a single-layer nonwoven fabric as disclosed herein can comprise a fiber web in an amount of from about 85 wt. % to about 99.99 wt. %, based on the total weight of the nonwoven fabric; and a cured natural binder in an amount of from about 0.01 wt. % to about 15 wt. %, based on the total weight of the nonwoven fabric; wherein the fiber web comprises natural fibers; wherein the natural fibers are present in the nonwoven fabric in an amount of from about 85 wt. % to about 99.99 wt. %, based on the total weight of the nonwoven fabric; wherein the cured natural binder comprises modified cellulose and a strengthening agent in a weight ratio of strengthening agent to modified cellulose of from about 1:2 to about 1:1,000, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof. In an aspect, a method of making a single-layer nonwoven fabric can comprise, for example, natural-bonded airlaid (NBAL) and/or cellulose-bonded airlaid (CBAL) techniques.

In an aspect, a method of making a nonwoven fabric as disclosed herein can generally comprise the steps of (a) forming a plurality of fibers into a fiber web; wherein the fiber web comprises natural fibers and synthetic fibers; wherein the natural fibers are present in the fiber web in an amount of from about 70 wt. % to about 90 wt. %, based on the total weight of the fiber web; and wherein the synthetic fibers are present in the fiber web in an amount of from about 10 wt. % to about 30 wt. %, based on the total weight of the fiber web; (b) contacting at least a portion of the fiber web with an aqueous natural binder to form a binder impregnated fiber web, wherein the aqueous natural binder comprises modified cellulose, a strengthening agent, and water, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof; and (c) curing the binder impregnated fiber web to form the nonwoven fabric; wherein the nonwoven fabric comprises the fiber web in an amount of from about 85 wt. % to about 99.99 wt. %, based on the total weight of the nonwoven fabric; and wherein the nonwoven fabric comprises a cured natural binder in an amount of from about 0.01 wt. % to about 15 wt. %, based on the total weight of the nonwoven fabric.

The terms used herein generally have their ordinary meanings in the art, within the context of this disclosure and in the specific context where each term is used. Certain terms are defined below to provide additional guidance in describing the compositions and methods of the current disclosure and how to make and use them.

As used in the specification and the appended claims, the singular forms "a," "an" and "the" include plural referents unless the context clearly dictates otherwise. Thus, for example, reference to "a compound" includes mixtures of compounds.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, alternatively up to 10%, alternatively up to 5%, or alternatively up to 1% of a given value. Alternatively, particularly with respect to systems or processes, the term can mean within an order of magnitude, within 5-fold, and within 2-fold, of a value.

As used herein, the term "weight percent" (wt. %) is meant to refer to either (i) the quantity by weight of a constituent or component in a material as a percentage of the weight of the material; or (ii) to the quantity by weight of a constituent or component in a material as a percentage of the weight of the final nonwoven material or product.

The term "basis weight" as used herein refers to the quantity by weight of a compound over a given area. Examples of the units of measure include grams per square meter ($g/m^2$) as identified by the acronym (gsm).

As used herein, the terms "gli," "g/in," and "G/in" refer to "grams per linear inch" or "gram force per inch." This refers to the width, not the length, of a test sample for tensile strength testing.

As used herein, "aqueous" means water and mixtures composed substantially of water.

As used herein, the terms "fiber," "fibrous" and the like are intended to encompass materials that have an elongated morphology exhibiting an aspect ratio (length to thickness) of greater than about 100, alternatively greater than about 500, alternatively greater than about 1,000, or alternatively greater than about 10,000.

The nonwovens as disclosed herein can be made by using any suitable methodology.

In some aspects, a method of making a nonwoven fabric as disclosed herein can comprise the step of forming a plurality of fibers into a fiber web; wherein the fiber web comprises natural fibers and synthetic fibers. In such aspects, the nonwoven fabric can be a multi-layer nonwoven fabric as disclosed herein, wherein the multi-layer nonwoven fabric comprises a multi-layer fiber web. The natural fibers can be present in the fiber web (e.g., multi-layer fiber web) in an amount of from about 50 wt. % to about 99 wt. %, alternatively from about 60 wt. % to about 95 wt. %, alternatively from about 70 wt. % to about 90 wt. %, alternatively from about 75 wt. % to about 85 wt. %, or alternatively from about 77.5 wt. % to about 82.5 wt. %, based on the total weight of the fiber web. The synthetic fibers can be present in the fiber web (e.g., multi-layer fiber web) in an amount of from about 1 wt. % to about 50 wt. %, alternatively from about 5 wt. % to about 40 wt. %, alternatively from about 10 wt. % to about 30 wt. %, alternatively from about 15 wt. % to about 25 wt. %, or alternatively from about 17.5 wt. % to about 22.5 wt. %, based on the total weight of the fiber web.

In other aspects, a method of making a nonwoven fabric as disclosed herein can comprise the step of forming a plurality of fibers into a fiber web; wherein the fiber web comprises natural fibers (and no synthetic fibers). In such aspects, the nonwoven fabric can be a single-layer nonwoven fabric, wherein the single-layer nonwoven fabric comprises a single-layer fiber web. The natural fibers can be present in the fiber web (e.g., single-layer fiber web) in an amount of 100 wt. %, based on the total weight of the fiber web. The fiber web (e.g., single-layer fiber web) can be substantially free of synthetic fibers. In such aspects, the fiber web (e.g., single-layer fiber web) can comprise, consist of, or consist essentially of natural fibers. In such aspects, the fiber web (e.g., single-layer fiber web) can exclude synthetic fibers.

As used herein, a "nonwoven," a "nonwoven material," or a "nonwoven fabric" refers to a sheet of fibers, continuous filaments, or chopped yarns of any nature or origin, that have been formed into a web by any means, and bonded together by at least the natural binder described herein, wherein weaving or knitting is not involved in forming and/or bonding the web. Further, for purposes of the disclosure herein, a "nonwoven," a "nonwoven material," or a "nonwoven fabric" refers to sheet or web structures made of fiber, filaments, molten plastic, or plastic films bonded together at least chemically (e.g., bonding with a cementing medium or binder, such as the natural binder as disclosed herein), although other types of bonding can be used for producing nonwovens, such as thermal bonding (e.g., fusing of the fibers, as in the case of thermoplastic fibers), mechanical bonding (e.g., mechanical interlocking of fibers in a random web or mat), etc. Web bonding processes impart integrity to the web and the resulting material is often referred to as fabric(s). Often, the fabrics can undergo further mechanical and/or chemical finishing or both in order to achieve enhanced properties and appearance. As will be appreciated by one of skill in the art, and with the help of this disclosure, all these processes along with the choice of fibers determine the structure and properties of the nonwoven fabrics.

A variety of processes can be used to assemble the nonwoven fabrics described herein, including but not limited to, traditional wet laying processes and dry forming processes such as air-laying and carding, or any other suitable forming technologies such as spunlace or airlaid. In an aspect, the nonwoven fabrics can be prepared by an airlaid process. Processes and equipment suitable for the production of nonwoven materials are described in more detail U.S. Pat. Nos. 4,335,066; 4,732,552; 4,375,448; 4,366,111; 4,375,447; 4,640,810; 206,632; 2,543,870; 2,588,533; 5,234,550; 4,351,793; 4,264,289; 4,666,390; 4,582,666; 5,076,774; 874,418; 5,566,611; 6,284,145; 6,363,580; and 6,726,461; each of which is incorporated by reference herein in its entirety.

In an aspect, the fiber web can be made by using any suitable methodology. Generally, a web forming process is a process that disperses the fibers or filaments to form a sheet or web (e.g., single-layer fiber web) and can also stack the webs to form multi-layer webs, which are sometimes referred to as batts. In an aspect, the multi-layer fiber web can comprise a first outer layer, a second outer layer, and optionally one or more intermediate layers, wherein the one or more intermediate layers are disposed between the first outer layer and the second outer layer.

In an aspect, the multi-layer web can comprise a first outer layer, a second outer layer, and optionally one or more intermediate layers, wherein each layer has a composition that is different from the composition of its adjacent layer(s).

In some aspects, the fibers can be arranged in a multi-layer web that has a concentration gradient of synthetic fibers across a thickness of the multi-layer web, as will be described in more detail herein. For example, fibers can be conveyed to one or more forming heads to deposit such fibers in a desired order to produce a multi-layer web with distinct strata (e.g., a multi-layer web that has a concentration gradient of synthetic fibers across a thickness of the multi-layer web).

In other aspects, one or more layers can be formed into distinct sheets or webs that can be combined to produce multi-layer webs, wherein the multi-layer webs have a concentration gradient of synthetic fibers across a thickness of the multi-layer webs. For example, one or more layers or webs can be prefabricated prior to being combined with additional layers. Each layer can use one or more forming heads to convey the desired amount and type of fibers to produce the desired layer composition.

Methods of forming multi-layer webs are described in more detail in U.S. Publication No. 20180001591 A; which is incorporated by reference herein in its entirety.

In some aspects, the step of forming a plurality of fibers into a fiber web (e.g., single-layer fiber web, multi-layer fiber web) can be a wet laid process. In other aspects, the step of forming a plurality of fibers into a fiber web (e.g., single-layer fiber web, multi-layer fiber web) can be a dry laid process. In yet other aspects, the step of forming a plurality of fibers into a fiber web (e.g., single-layer fiber web, multi-layer fiber web) can be a spunlaid process.

Generally, techniques for wet laying fibrous material to form sheets, such as dry lap and paper, are well known in the art. Suitable wet laying techniques include, but are not limited to, hand sheeting and wet laying with paper making machines as disclosed in U.S. Pat. No. 3,301,746, which is incorporated by reference herein in its entirety. The principle of wet laying is similar to paper manufacturing. The difference lies in the amount of synthetic fibers present in a wet laid nonwoven material. A dilute slurry of water and fibers can be deposited on a moving wire screen and drained to form a web. The web (e.g., single-layer fiber web, multi-layer fiber web) can be further dewatered, consolidated, by pressing between rollers, and dried. Impregnation with binders (e.g., natural binder) can follow the web forming process. The strength of a randomly oriented web (e.g., single-layer fiber web, multi-layer fiber web) is rather similar in all directions in the plane of the fabric for wet laid nonwovens.

The dry laid process can include a mechanical process known as carding, which is described in more detail in U.S. Pat. No. 797,749, which is incorporated by reference herein in its entirety. The carding process can include an airstream component to randomize the orientation of fibers when they are collected on a forming wire. Typically, the fiber length for a mechanically carded process can be in the range of 38-60 mm. Longer fiber lengths can be possible depending on the set up of the card. Some mechanical cards, such as the Truzschler-Fliessner EWK-413 card, can run fibers having significantly shorter length than 38 mm.

In an aspect, the dry laid process can comprise an airlaid process (e.g., air-forming process). The airlaid process employs only air flow, gravity, and centripetal force to deposit a stream of fibers onto a moving forming wire that conveys the fiber web (e.g., single-layer fiber web, multi-layer fiber web) to a web bonding process (e.g., chemical bonding with a natural binder). The airlaid process is effective at forming a uniform web (e.g., single-layer fiber web, multi-layer fiber web) of short fibers, e.g., typically less than 6 mm long, with low fiber to fiber cohesion and low potential for generating static. The dominant fiber utilized in these air driven processes is wood pulp, which can be processed at high throughput owing to its short length of 3 mm or less. Typically, fiber lengths above 12 mm are commercially impractical for airlaid processes. Pulp-based air-formed nonwoven webs can incorporate thermoplastic fibers that could melt and additionally bond the airlaid web together when the air-formed web is heated, for example by passing through ovens. Without wishing to be limited by theory, it is possible to air-form a layer of 100% thermoplastic fiber; however, the fiber throughput rate typically declines significantly with increasing fiber length. Airlaid processes are described in more detail in U.S. Pat. Nos. 4,014,635 and 4,640,810; each of which is incorporated by reference herein in its entirety.

Generally, spunlaid (also known as spunbond or spunbonded) and meltblown processes are types of spunmelt processes, where "spunmelt" is a generic term describing the manufacturing of nonwoven fiber webs directly from thermoplastic polymers. During spunlaid processes, polymer granules can be melted, and molten polymer can be extruded through spinnerets, resulting in continuous polymeric filaments that are then cooled and deposited onto a conveyor to form a fiber web. While the temperature of the polymeric filaments can cause them to adhere to one another on the conveyor, such bonding is generally insufficient, and the spunlaid fiber webs require further bonding, for example by using a natural binder as disclosed herein.

In an aspect, the plurality of fibers can comprise natural fibers (e.g., cellulosic or cellulose fibers), synthetic fibers, or both. Any cellulosic fibers known in the art, including cellulose fibers of any natural origin, such as those derived from wood pulp, may be used for forming the web. Nonlimiting examples of natural fibers suitable for use in the present disclosure for forming the web include, but are not limited to, wood cellulose; cotton linter pulp; cellulosic fibers; modified cellulose (e.g., modified cellulosic fibers); chemically modified cellulose (e.g., chemically treated cellulosic fibers), such as crosslinked cellulosic fibers; highly purified cellulosic fiber; digested cellulosic fibers, such as kraft digested fibers, prehydrolyzed kraft digested cellulosic fibers, soda digested cellulosic fibers, sulfite digested cellulosic fibers; chemi-thermally treated cellulosic fibers, mechanically treated cellulosic fibers, thermo-mechanically treated cellulosic fibers; cellulosic fibers derived from softwoods, such as pines, firs, and spruces; cellulosic fibers derived from hardwood, such as *eucalyptus*; cellulosic fibers derived from Esparto grass, bagasse, kemp, flax, hemp, kenaf, and other lignaceous and cellulosic fiber sources; and the like; or combinations thereof. Nonlimiting examples of natural fibers suitable for use in the present disclosure for forming the web include FOLEY FLUFFS fibers, which are bleached Kraft southern pine fibers available from Georgia-Pacific; cellulose pulp fibers, which are a southern softwood fluff pulp available from Georgia-Pacific; HPF, which is a highly purified cellulose fiber available from Georgia-Pacific; FFLE fibers, which are bleached and debonder-treated Southern softwood Kraft available from Georgia-Pacific; viscose or rayon fibers, which are produced from regenerated cellulose fiber; lyocell fibers, which is a form of rayon formed from dissolving pulp (bleached wood pulp) using dry jet-wet spinning; TENCEL cellulosic fibers, which is a type of lyocell fibers that is produced from wood, and are available from Lenzing; and T 730 hardwood pulp, which is an *eucalyptus* pulp available from Weyerhaeuser.

In an aspect, the cellulosic fibers comprise chemically treated cellulosic fibers. In some aspects, the chemically treated cellulose fibers can comprise crosslinked cellulosic fibers; polyhydroxy compound-treated cellulosic fibers; cellulosic fibers treated with a polyvalent cation-containing compound (e.g., polyvalent metal ion salt); and the like; or combinations thereof.

Nonlimiting examples of polyhydroxy compounds suitable for treating cellulosic fibers include glycerol, trimethylolpropane, pentaerythritol, polyvinyl alcohol, partially hydrolyzed polyvinyl acetate, fully hydrolyzed polyvinyl acetate, and the like, or combinations thereof.

Any suitable polyvalent metal ions can be used for treating cellulosic fibers. Nonlimiting examples of polyvalent metal ions suitable for treating cellulosic fibers include transition metals, beryllium, magnesium, calcium, strontium, barium, titanium, zirconium, vanadium, chromium, molybdenum, tungsten, manganese, iron, cobalt, nickel, copper, zinc, aluminum, tin, and the like, or combinations thereof.

Any suitable polyvalent metal ion salts can be used for treating cellulosic fibers. Polyvalent metal ion salts suitable for treating cellulosic fibers comprise salts (e.g., chlorides, nitrates, sulfates, borates, bromides, iodides, fluorides, nitrides, perchlorates, phosphates, hydroxides, sulfides, carbonates, bicarbonates, oxides, alkoxides phenoxides, phosphites, hypophosphites, formates, acetates, butyrates, hexanoates, adipates, citrates, lactates, oxalates, propionates, salicylates, glycinates, tartrates, glycolates, sulfonates, phosphonates, glutamates, octanoates, benzoates, gluconates, maleates, succinates, 4,5-dihydroxy-benzene-1,3-disulfonates, and the like, or combinations thereof) of polyvalent metal ions (e.g., transition metals, beryllium, magnesium, calcium, strontium, barium, titanium, zirconium, vanadium, chromium, molybdenum, tungsten, manganese, iron, cobalt, nickel, copper, zinc, aluminum, tin, and the like, or combinations thereof). Complexes of polyvalent metal ion salts with any suitable complexing agents (e.g., amines, ethylenediaminetetra-acetic acid (EDTA), diethylenetriaminepenta-acetic acid (DIPA), nitrilotri-acetic acid (NTA), 2,4-pentanedione, ammonia, and the like, or combinations thereof) can also be used for treating cellulosic fibers.

Chemically treated cellulosic fibers and methods of making same are described in more detail in U.S. Pat. Nos. 5,492,759; 5,601,921; and 6,159,335; each of which is incorporated by reference herein in its entirety.

In aspects where the fiber web comprises natural fibers, the nonwoven fabric (e.g., single-layer nonwoven fabric) can be characterized by a degree of biodegradability of equal to or greater than about 99%, alternatively equal to or greater than about 99.5%, or alternatively equal to or greater than about 99.9%, wherein the degree of biodegradability refers to aerobic biodegradability in soil as determined in accordance with ISO 17556:2003 E. In such aspects, the fiber web (e.g., single-layer fiber web) can comprise, consist of, or consist essentially of natural fibers. In such aspects, the fiber web (e.g., single-layer fiber web) can exclude synthetic fibers. Generally, the term "biodegradable" refers to a material that is capable of degrading or decaying through the action of living organisms, such as bacteria, fungi, etc. In an aspect, the fiber web (e.g., single-layer fiber web) can be characterized by a degree of biodegradability of 100%, wherein the degree of biodegradability refers to aerobic biodegradability in soil as determined in accordance with ISO 17556:2003 E.

In an aspect, the fiber web (e.g., single-layer fiber web) can comprise natural fibers, wherein the natural fibers comprise biodegradable cellulosic fibers. In such aspect, the fiber web (e.g., single-layer fiber web) can comprise, consist of, or consist essentially of biodegradable cellulosic fibers.

In an aspect, the plurality of fibers can comprise synthetic fibers. Nonlimiting examples of synthetic fibers suitable for use in the present disclosure for forming the web include acrylic polymers, polyamides (e.g., Nylon 6, Nylon 6/6, Nylon 12, polyaspartic acid, polyglutamic acid, etc.), polyamines, polyimides, polyacrylics (e.g., polyacrylamide, polyacrylonitrile, esters of methacrylic acid and acrylic acid, etc.), polycarbonates (e.g., polybisphenol A carbonate, polypropylene carbonate, etc.), polydienes (e.g., polybutadiene, polyisoprene, polynorbornene, etc.), polyepoxides, polyesters (e.g., polyethylene terephthalate, polybutylene terephthalate, polytrimethylene terephthalate, polycaprolactone, polyglycolide, polylactide, polyhydroxybutyrate, polyhydroxyvalerate, polyethylene adipate, polybutylene adipate, polypropylene succinate, etc.), polyethers (e.g., polyethylene glycol (polyethylene oxide), polybutylene glycol, polypropylene oxide, polyoxymethylene (paraformaldehyde), polytetramethylene ether (polytetrahydrofuran), polyepichlorohydrin, etc.), polyfluorocarbons, formaldehyde polymers (e.g., urea-formaldehyde, melamine-formaldehyde, phenol formaldehyde), natural polymers (e.g., cellulosics, chitosans, lignins, waxes, etc.), polyolefins (e.g., polyethylene, polypropylene, polybutylene, polybutene, polyoctene, etc.), polyphenylenes (e.g., polyphenylene oxide, polyphenylene sulfide, polyphenylene ether sulfone, etc.), silicon containing polymers (e.g., polydimethyl siloxane, polycarbomethyl silane, etc.), polyurethanes, polyvinyls (e.g., polyvinyl butyral, polyvinyl alcohol, esters and ethers of polyvinyl alcohol, polyvinyl acetate, polystyrene, polymethylstyrene, polyvinyl chloride, polyvinyl pryrrolidone, polymethyl vinyl ether, polyethyl vinyl ether, polyvinyl methyl ketone, etc.), polyacetals, polyarylates, and copolymers (e.g., polyethylene-co-vinyl acetate, polyethylene-co-acrylic acid, polybutylene terephthalate-co-polyethylene terephthalate, polylauryllactam-block-polytetrahydrofuran, etc.), polylactic acid (PLA) based polymers, polybutylene succinate (PBS) based polymers, derivatives thereof, copolymers thereof, and the like, or combinations thereof.

In some aspects, the fiber web can comprise natural fibers (which are biodegradable) and biodegradable synthetic fibers, such as PLA-based polymeric fibers and/or PBS-based polymeric fibers. In an aspect, the biodegradable synthetic fibers (e.g., PLA-based polymeric fibers and/or PBS-based polymeric fibers) can be characterized by a degree of biodegradability of equal to or greater than about 99%, alternatively equal to or greater than about 99.5%, or alternatively equal to or greater than about 99.9%, wherein the degree of biodegradability refers to aerobic biodegradability in soil as determined in accordance with ISO 17556:2003 E. In such aspects, the biodegradable synthetic fibers (e.g., PLA-based polymeric fibers and/or PBS-based polymeric fibers) can be characterized by a degree of biodegradability of 100%, wherein the degree of biodegradability refers to aerobic biodegradability in soil as determined in accordance with ISO 17556:2003 E. In aspects where the fiber web comprises natural fibers and biodegradable synthetic fibers (e.g., PLA-based polymeric fibers and/or PBS-based polymeric fibers), the nonwoven fabric (e.g., multi-layer nonwoven fabric) and the fiber web (e.g., multi-layer fiber web) can be characterized by a degree of biodegradability of equal to or greater than about 99%, alternatively equal to or greater than about 99.5%, or alternatively equal to or greater than about 99.9%, wherein the degree of biodegradability refers to aerobic biodegradability in soil as determined in accordance with ISO 17556:2003 E. In such aspects, the nonwoven fabric (e.g., multi-layer nonwoven fabric) and the fiber web (e.g., multi-layer fiber web) can be characterized by a degree of biodegradability of 100%, wherein the degree of biodegradability refers to aerobic biodegradability in soil as determined in accordance with ISO 17556:2003 E.

In aspects where the fiber web comprises natural fibers and non-biodegradable synthetic fibers, the nonwoven fabric (e.g., multi-layer nonwoven fabric) can be non-biodegradable. In such aspects, the non-biodegradable synthetic fibers can comprise polyethylene terephthalate (PET) and/or polyethylene (PE). For example, non-biodegradable synthetic fibers can comprise bicomponent fibers comprising PET and/or PE as disclosed herein. Generally, the term "non-biodegradable" refers to a material that is not capable of degrading or decaying through the action of living organisms, such as bacteria, fungi, etc.

In an aspect, the synthetic fibers can comprise monocomponent fibers (i.e., single synthetic polymer or copolymer component in the fibers), bicomponent fibers (i.e., two synthetic polymer or copolymer components in the fibers), multicomponent fibers (i.e., more than two synthetic polymer or copolymer components in the fibers), or combinations thereof.

In some aspects, the synthetic fibers can comprise monocomponent fibers, wherein the monocomponent fibers can comprise polyethylene, polypropylene, polyester, polylactic acid, and the like, or combinations thereof.

In some aspects, the synthetic fibers can comprise multicomponent fibers, for example multicomponent fibers having enhanced reversible thermal properties. Generally, multicomponent fibers contain temperature regulating materials, such as phase change materials having the ability to absorb or release thermal energy to reduce or eliminate heat flow. In general, a phase change material can comprise any substance, or mixture of substances, that has the capability of absorbing or releasing thermal energy to reduce or eliminate heat flow at or within a temperature stabilizing range. The temperature stabilizing range may comprise a particular transition temperature or range of transition temperatures. A phase change material used in nonwoven fabrics as disclosed herein can inhibit a flow of thermal energy during a time when the phase change material is absorbing or releasing heat, typically as the phase change material undergoes a transition between two states, such as, for example, liquid and solid states, liquid and gaseous states, solid and gaseous states, or two solid states. Phase changing is typically transient, and will occur until a latent heat of the phase change material is absorbed or released during a heating or cooling process. Thermal energy may be stored or removed from the phase change material, and the phase change material typically can be effectively recharged by a source of heat or cold. By selecting an appropriate phase change material, the multi-component fiber may be designed for use in any one of numerous products. Multicomponent fibers having enhanced reversible thermal properties are described in more detail in U.S. Pat. No. 6,855,422, which is incorporated by reference herein in its entirety.

In some aspects, the synthetic fibers can comprise bicomponent fibers. Generally, bicomponent fibers can have a core and a sheath surrounding the core, wherein the core and the sheath comprise different polymers. For example, the core comprises a first polymer, and the sheath comprises a second polymer, wherein the first polymer and the second polymer are different (e.g., the first polymer and the second polymer have different melting temperatures). Bicomponent fibers are typically used for producing nonwoven materials by airlaid techniques.

Bicomponent fibers may incorporate a variety of polymers as their core and sheath components. Bicomponent fibers that have a PE or modified PE sheath typically have a PET or polypropylene (PP) core. In an aspect, the bicomponent fiber can have a core made of polyester and a sheath made of polyethylene.

In an aspect, bicomponent fibers can have a length of equal to or greater than about 6 mm, alternatively equal to or greater than about 8 mm, alternatively equal to or greater than about 10 mm, alternatively equal to or greater than about 12 mm, alternatively from about 3 mm to about 36 mm, alternatively from about 4 mm to about 24 mm, alternatively from about 5 mm to about 18 mm, or alternatively from about 6 mm to about 12 mm. The bicomponent fibers suitable for use in the present disclosure can have any suitable geometry, such as concentric, eccentric, side by side, islands in a sea, pie segments and other variations.

Various degrees of stretching, drawing or draw ratios can be used for the bicomponent fibers suitable for use in the present disclosure, including partially drawn and highly drawn bicomponent fibers and homopolymers. These fibers can include a variety of polymers and may have a partially drawn core, a partially drawn sheath or a partially drawn core and sheath, or they may be a homopolymer that is partially drawn. In some aspects, the bicomponent fibers can have a partially drawn core. Highly drawn bicomponent fibers are described in more detail later herein.

The bicomponent fibers suitable for use in the present disclosure can include fibers that utilize a partially drawn polyester core with a variety of sheath materials, specifically including a polyethylene sheath. The use of both partially drawn and highly drawn bicomponent fibers in the same structure can be leveraged to meet specific physical and performance properties based on how the fibers are incorporated into the structure. The degree to which the partially drawn bicomponent fibers are drawn is not limited in scope as different degrees of drawing will yield different enhancements in performance. The scope of the partially drawn bicomponent fibers encompasses fibers with various core sheath configurations including, but not limited to concentric, eccentric, side by side, islands in a sea, pie segments and other variations. In addition, the bicomponent fibers can comprise partially drawn homopolymers such as polyester, polypropylene, nylon, and other melt spinnable polymers. A nonlimiting example of partially drawn core bicomponent fibers suitable for use in the present disclosure include TREVIRA T265 bicomponent fibers, which are partially drawn core with a core made of polybutylene terephthalate (PBT) and a sheath made of polyethylene, and which are available from Trevira, Bobingen, Germany.

As used herein, the term "partially drawn core" or "partially drawn fiber" refers to all or part of a fiber, such as with a bicomponent fiber, that has not been drawn or stretched to achieve the highest possible tenacity or strength in its fiber form, but that some degree of drawing or stretching has been done to induce some degree of orientation or crystallinity and strength into the fiber. As such, a partially drawn core bicomponent fiber or a partially drawn homopolymer can still be capable of being stretched or drawn further once incorporated into an article. This allows the partially drawn core bicomponent fiber or partially drawn homopolymer to provide additional strength and elongation to the article as it is further drawn while incorporated within an article. A homopolymer or bicomponent fiber can be typically stretched close to the point of failure as this induces a high level of crystallinity and strength into the fiber form. The drawing or stretching of a filament, before it is cut into fibers, can occur in both the spinning and drawing steps. Drawing during the spinning step, also known as "drawdown," occurs when the molten fiber is pulled from the face of a spinneret resulting in drawing of the spun filament. Some degree of drawing is required in order to prevent the as-spun filament from becoming embrittled due to aging, which can cause a catastrophic failure, such as breaking, during the drawing step. Spinning and drawing homopolymer and bicomponent fibers are disclosed in more detail in U.S. Pat. Nos. 4,115,989; 4,217,321; 4,529,368; 4,687,610; 5,185,199; 5,372,885; and 6,841,245; each of which is incorporated by reference herein in its entirety. Some fibers, yarns and other melt spun or extruded materials can be referred to as undrawn, but still have some drawing during the melt spinning phase where the polymer is pulled away from the face of the spinneret. Some other fibers, yarns and other melt spun or extruded materials where no tension is applied to the fibers as they leave the face of the spinneret, for example adhesive polymers, can also be referred to as undrawn. Undrawn polymeric fibers suitable for use in the present disclosure are disclosed in more detail in U.S. Pat. Nos. 3,931,386, 4,021,410, 4,237,187, 4,434,204, 4,609,710, 5,229,060, 5,336,709, 5,634,249, 5,660,804, 5,773,825, 5,811,186, 5,849,232, 5,972,463, and 6,080,482, each of which is incorporated by reference herein in its entirety.

In an aspect, the bicomponent fibers can comprise highly drawn bicomponent fibers. As used herein, "highly drawn" is defined as being drawn or stretched close to the maximum level of drawing or stretching such that it will induce a high degree of molecular orientation in the fiber, and enhanced strength in the fiber form, without overdrawing or overstretching such that the fiber has a catastrophic failure and potentially breaks. In an aspect, the bicomponent fibers can comprise bicomponent fibers that are partially drawn with varying degrees of draw or stretch; highly drawn bicomponent fibers; and mixtures thereof. Nonlimiting examples of highly drawn bicomponent fibers suitable for use in the present disclosure include INVISTA T255 bicomponent fibers and TREVIRA T255 bicomponent fibers, which are highly drawn polyester core bicomponent fibers with a variety of sheath materials, specifically including a polyethylene sheath, and which are available from Invista, Salisbury, NC, and Trevira, Bobingen, Germany, respectively; and AL-Adhesion-C bicomponent fibers, which are highly drawn polypropylene core bicomponent fiber with a variety of sheath materials, specifically including a polyethylene sheath, which are available from ES FiberVisions, Varde, Denmark.

Bicomponent fibers suitable for use in the present disclosure are described in more detail in U.S. Pat. Nos. 5,372,885 and 5,456,982, each of which is incorporated by reference herein in its entirety. Processes for producing bicomponent fibers are described in more detail in U.S. Pat. Nos. 4,950, 541, 5,082,899, 5,126,199, 5,372,885, 5,456,982, 5,705,565, 2,861,319, 2,931,091, 2,989,798, 3,038,235, 3,081,490, 3,117,362, 3,121,254, 3,188,689, 3,237,245, 3,249,669, 3,457,342, 3,466,703, 3,469,279, 3,500,498, 3,585,685, 3,163,170, 3,692,423, 3,716,317, 3,778,208, 3,787,162, 3,814,561, 3,963,406, 3,992,499, 4,052,146, 4,251,200, 4,350,006, 4,370,114, 4,406,850, 4,445,833, 4,717,325, 4,743,189, 5,162,074, 5,256,050, 5,505,889, 5,582,913, and 6,670,035, each of which is incorporated by reference herein in its entirety.

In an aspect, a method of making the nonwoven fabric as disclosed herein can comprise a step of contacting at least a portion of the fiber web with an aqueous natural binder to form a binder impregnated fiber web. The fiber web can be contacted with the aqueous natural binder by using any suitable methodology. In an aspect, the aqueous natural binder can be contacted with (e.g., applied to) the fiber web via a saturation bonding method, a foam bonding method, a spray bonding method, a print bonding method, and the like, or combinations thereof. The aqueous natural binder can also be referred to as "aqueous cellulosic binder," and the terms "aqueous natural binder" and "aqueous cellulosic binder" can be used interchangeably for purposes of the disclosure herein. Further, the terms "natural binder" and "cellulosic binder" can be used interchangeably for purposes of the disclosure herein.

In an aspect, the aqueous natural binder can comprise modified cellulose, a strengthening agent, and water, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof.

In an aspect, the aqueous natural binder can comprise modified cellulose, wherein the modified cellulose comprises CMC and/or sodium CMC. CMC and sodium CMC are cellulose derivatives (i.e., modified cellulose). Cellulose is a fibrous carbohydrate found in plants, and is the structural component of plant cell walls. Cellulose is considered the most abundant naturally occurring organic polymer on Earth; accounting for over half of all the carbon found in the plant kingdom. Cellulose is a polysaccharide, and is a linear polymer of glucose consisting of a linear chain of hundreds to thousands of D-glucose units that are linked by β-1,4-glycosidic linkages. CMC is a chemically modified derivative of cellulose, and is generally formed by reaction of cellulose with alkali and chloroacetic acid. Each repeating glucose unit in CMC has three hydroxyl groups (—OH), each of which, and without wishing to be limited by theory, could be substituted with carboxymethyl groups (—CH$_2$—COOH) to form the corresponding carboxymethyl ethers (—O—CH$_2$—COOH). However, based on the cellulose starting material, and on the reaction conditions, only some of the hydroxyl groups in the cellulose polymer chain end up substituted with carboxymethyl groups, and the average number of hydroxyl groups substituted per glucose monomeric unit is known as the degree of substitution. The properties (e.g., solubility, viscosity) of the CMC are dependent upon the length of the polymeric chain, as well as upon the degree of substitution. Generally, CMC is commercially available with a degree of substitution of from about 0.3 to about 2, most commonly from about 0.6 to about 0.9. As will be appreciated by one of skill in the art, and with the help of this disclosure, and without wishing to be limited by theory, the pKa of CMC depends on the degree of substitution, and for the most commonly available CMC (e.g., degree of substitution from about 0.6 to about 0.9), the pKa is about 4-5, being similar to the pKa of acetic acid. Further, and as will be appreciated by one of skill in the art, and with the help of this disclosure, and without wishing to be limited by theory, depending on the pH of the solution used for obtaining the carboxymethylcellulose, the CMC could be fully protonated (e.g., pH values below the pKa, such as a pH of 1-2); the CMC could be fully deprotonated, and as such it would be sodium CMC (e.g., pH values above the pKa, such as a pH of 7); or the CMC could be partially protonated and partially deprotonated (e.g., sodium salt) at pH values around the pKa. Sodium CMC comprise at least a portion of the carboxymethyl ether groups in sodium salt form (—O—CH$_2$—COO$^-$Na$^+$).

CMC and sodium CMC can be used in foods, cosmetics, and even in pharmaceutics, owing to being biocompatible, biodegradable, and non-toxic.

Without wishing to be limited by theory, modified cellulose (e.g., CMC and/or sodium CMC) can form hydrogen bonds with nonwoven fibers (e.g., cellulosic fiber), as well as covalent bonds, such as ester type bonds, thereby increasing the strength of nonwovens.

Nonlimiting examples of commercially available CMC and sodium CMC suitable for use in the present disclosure include AQUALON sodium CMC available from Ashland; GELYCEL CMC available from Amtex; WALOCEL CMC available from Dow; and the like; or combinations thereof.

In an aspect, the aqueous natural binder can comprise the modified cellulose in an amount of from about 0.1 wt. % to about 50 wt. %, alternatively from about 1 wt. % to about 40 wt. %, or alternatively from about 2.5 wt. % to about 25 wt. %, based on the total weight of the aqueous natural binder.

In an aspect, the aqueous natural binder can comprise a strengthening agent, wherein the strengthening agent comprises a crosslinking agent and/or a wet strength agent. For purposes of the disclosure herein, the term "strengthening agent" refers to a compound that can improve the strength (e.g., tensile strength) properties of nonwoven materials. The strengthening agent can also be referred to as a "binder modifier," and the terms "strengthening agent" and "binder modifier" can be used interchangeably for purposes of the disclosure herein.

In an aspect, the aqueous natural binder can comprise the strengthening agent in an amount of from about 0.1 wt. % to about 10 wt. %, alternatively from about 0.5 wt. % to about 5 wt. %, or alternatively from about 1 wt. % to about 2.5 wt. %, based on the total weight of the aqueous natural binder.

In an aspect, the aqueous natural binder can comprise modified cellulose and strengthening agent in a weight ratio of strengthening agent to modified cellulose of from about 1:2 to about 1:1,000, alternatively from about 1:3 to about 1:750, alternatively from about 1:4 to about 1:500, or alternatively from about 1:5 to about 1:100.

In an aspect, the strengthening agent comprises a crosslinking agent, wherein the crosslinking agent comprises a carboxylic acid having two or more carboxyl groups. Nonlimiting examples of carboxylic acids having two or more carboxyl groups suitable for use as crosslinking agent in the present disclosure include citric acid, oxalic acid, malonic acid, succinic acid, glutaric acid, adipic acid, malic acid, polyacrylic acid, and the like, or combinations thereof. In an aspect, the crosslinking agent comprises citric acid. As will be appreciated by one of skill in the art, and with the help of this disclosure, the crosslinking agents disclosed herein can be used in foods, cosmetics, and even in pharmaceutics, owing to being biocompatible, biodegradable, and non-toxic.

Without wishing to be limited by theory, the crosslinking agent of the type disclosed herein comprises carboxyl groups which can form covalent bonds (e.g., ester type bonds), as well as hydrogen bonds and/or ionic bonds, with both nonwoven fibers (e.g., cellulosic fibers, natural fibers), and/or with the modified cellulose, thereby providing nonwovens with increased wet strength and/or increased dry strength.

In an aspect, the aqueous natural binder can comprise the crosslinking agent in an amount of from about 0.1 wt. % to about 10 wt. %, alternatively from about 0.5 wt. % to about 5 wt. %, or alternatively from about 1 wt. % to about 2.5 wt. %, based on the total weight of the aqueous natural binder.

In an aspect, the aqueous natural binder can comprise modified cellulose and crosslinking agent in a weight ratio of crosslinking agent to modified cellulose of from about 1:2 to about 1:1,000, alternatively from about 1:3 to about 1:750, alternatively from about 1:4 to about 1:500, or alternatively from about 1:5 to about 1:100. In some aspects, the aqueous natural binder can comprise modified cellulose and crosslinking agent in a weight ratio of crosslinking agent to modified cellulose of about 1:2.5.

In an aspect, the strengthening agent comprises a wet strength agent. In an aspect, the wet strength agent can comprise at least one reactive functional group selected from the group consisting of a halide group, a chloride group, a fluoride group, a hydroxyl group, and combinations thereof. Generally, a wet strength agent can be used in nonwovens to improve strength properties of nonwoven materials. Without wishing to be limited by theory, a wet strength agent of the type disclosed herein can form chemical bonds (e.g., covalent bonds, ionic bonds) with the modified cellulose and/or nonwoven fibers, for example via the at least one reactive functional group, thereby improving the strength of nonwovens. For purposes of the disclosure herein, the term "reactive functional group" refers to a functional group that can undergo a reaction to form chemical bonds (e.g., covalent bonds, ionic bonds) with the modified cellulose and/or nonwoven fibers, for example under the conditions of treating the fiber web with the natural binder, curing the binder, etc.

Nonlimiting examples of a wet strength agent suitable for use in the present disclosure include N-methylolacrylamide (NMA), polyacrylamide (PAM), glyoxylated polyacrylamide (GPAM), polyamide epichlorohydrin (PAE), polyamidoamine epichlorohydrin (PAAE), and the like, or combinations thereof.

Nonlimiting examples of commercially available wet strength agent suitable for use in the present disclosure include POLYCUP crosslinking resins, which are formaldehyde-free, water-based resins that are reactive with amine, carboxyl, hydroxyl and thiol functionality, and which are available from Solenis; FENNOBOND bonding agent available from Kemira; and the like; or combinations thereof.

In an aspect, the aqueous natural binder can comprise the wet strength agent in an amount of from about 0.1 wt. % to about 10 wt. %, alternatively from about 0.5 wt. % to about 5 wt. %, or alternatively from about 1 wt. % to about 2.5 wt. %, based on the total weight of the aqueous natural binder.

In some aspects, the aqueous natural binder can comprise POLYCUP crosslinking resin in an amount of from about 0.1 wt. % to about 0.5 wt. %, or alternatively from about 0.2 wt. % to about 0.3 wt. %, based on the total weight of the aqueous natural binder.

In an aspect, the aqueous natural binder can comprise modified cellulose and wet strength agent in a weight ratio of wet strength agent to modified cellulose of from about 1:2 to about 1:1,000, alternatively from about 1:3 to about 1:750, alternatively from about 1:4 to about 1:500, or alternatively from about 1:5 to about 1:100. In some aspects, the aqueous natural binder can comprise modified cellulose and wet strength agent in a weight ratio of wet strength agent to modified cellulose of about 1:2.5.

In an aspect, the aqueous natural binder can comprise any suitable binder additive, such as a softening agent, an electrolyte, and the like, or combinations thereof.

In an aspect, the aqueous natural binder can further comprise a softening agent in an amount of from about 0.1 wt. % to about 10 wt. %, alternatively from about 0.5 wt. % to about 5 wt. %, or alternatively from about 1 wt. % to about 2.5 wt. %, based on the total weight of the aqueous natural binder.

Generally, a softening agent can be used in nonwovens to provide specific softness, hydrophilicity, antistatic properties, etc. As will be appreciated by one of skill in the art, and with the help of this disclosure, softening agents can also reduce the water absorbency of nonwovens.

Nonlimiting examples of a softening agent suitable for use in the present disclosure include an anionic surfactant, glycerol, a polyethylene emulsion, ethylene glycol, polyethylene glycol, propylene glycol, polypropylene glycol, a fatty alcohol ethoxylate, sodium lauryl sulfate, a silicone-based softener, a nanomaterials-based softener, and the like, or combinations thereof.

In an aspect, the aqueous natural binder as disclosed herein can comprise modified cellulose, a strengthening agent, and a softening agent. In some aspects, the aqueous natural binder as disclosed herein can comprise modified cellulose, a crosslinking agent, and a softening agent. In other aspects, the aqueous natural binder as disclosed herein can comprise modified cellulose, a wet strength agent, and a softening agent. In yet other aspects, the aqueous natural binder as disclosed herein can comprise modified cellulose, a crosslinking agent, a wet strength agent, and a softening agent.

In an aspect, the aqueous natural binder can comprise strengthening agent and softening agent in a weight ratio of softening agent to strengthening agent of from about 1:10 to about 2:1, alternatively from about 1:5 to about 1.5:1, or alternatively from about 1:2 to about 1:1. In some aspects, the natural binder can comprise strengthening agent and softening agent in a weight ratio of softening agent to strengthening agent of about 1:1.

In some aspects, the aqueous natural binder can comprise modified cellulose, strengthening agent and softening agent in a weight ratio of modified cellulose to strengthening agent to softening agent of about 2.5:1:1, wherein the strengthening agent comprises a crosslinking agent, a wet strength agent, or both a crosslinking agent and a wet strength agent. In some aspects, the aqueous natural binder can comprise modified cellulose, crosslinking agent and softening agent in a weight ratio of modified cellulose to crosslinking agent to softening agent of about 2.5:1:1. In other aspects, the aqueous natural binder can comprise modified cellulose, wet strength agent and softening agent in a weight ratio of modified cellulose to wet strength agent to softening agent of about 2.5:1:1.

In an aspect, the aqueous natural binder can further comprise an electrolyte in an amount of from about 0.01 wt. % to about 0.5 wt. %, alternatively from about 0.02 wt. % to about 0.3 wt. %, or alternatively from about 0.05 wt. % to about 0.1 wt. %, based on the total weight of the aqueous natural binder. Generally, an electrolyte can decrease the viscosity of an aqueous solution of modified cellulose.

Nonlimiting examples of an electrolyte suitable for use in the present disclosure include NaCl, KCl, $CaCl_2$, $MgCl_2$, $AlCl_3$, $Na_2SO_4$, $Al_2SO_4$, $K_2SO_4$, $CaSO_4$, alum (KAl$(SO_4)_2 \cdot 12H_2O$), and the like, or combinations thereof.

In an aspect, the aqueous natural binder comprises modified cellulose, a strengthening agent, and water. In an aspect, the aqueous natural binder can be a sprayable aqueous solution. As will be appreciated by one of skill in the art, and with the help of this disclosure, if any of the components used for preparing the aqueous natural binder contain water (e.g., modified cellulose solution, strengthening agent aqueous solution), such water will be present in the aqueous natural binder, and will contribute to the total amount of water in the final aqueous natural binder composition.

In an aspect, the aqueous natural binder can be characterized by a weight ratio of water to modified cellulose of from about 99.9:0.1 to about 1,000:500 (i.e., from about 999:1 to about 2:1), alternatively from about 99:1 to about 500:100 (i.e., from about 99:1 to about 5:1), or alternatively from about 50:1 to about 100:10 (i.e., from about 50:1 to about 10:1).

In an aspect, the aqueous natural binder can have a pH of from about 2 to about 8, alternatively from about 3 to about 6, or alternatively from about 4 to about 5.

In an aspect, the aqueous natural binder as disclosed herein can be biodegradable.

In some aspects, the aqueous natural binder can be characterized by a degree of biodegradability of equal to or greater than about 99%, alternatively equal to or greater than about 99.5%, or alternatively equal to or greater than about 99.9%, wherein the degree of biodegradability refers to aerobic biodegradability in soil as determined in accordance with ISO 17556:2003 E. In an aspect, the aqueous natural binder can be characterized by a degree of biodegradability of 100%, wherein the degree of biodegradability refers to aerobic biodegradability in soil as determined in accordance with ISO 17556:2003 E.

In an aspect, the aqueous natural binder can be made by using any suitable methodology.

In an aspect, a method of making an aqueous natural binder can comprise a step of contacting modified cellulose (e.g., CMC and/or sodium CMC) with water to form a modified cellulose solution. The modified cellulose solution can be prepared by combining the modified cellulose with water in any suitable order. The modified cellulose solution can have a pH of from about 4 to about 8, alternatively from about 5 to about 7, or alternatively from about 6 to about 7.

In an aspect, the modified cellulose solution can comprise the modified cellulose in an amount of from about 0.1 wt. % to about 50 wt. %, alternatively from about 1 wt. % to about 40 wt. %, or alternatively from about 2.5 wt. % to about 25 wt. %, based on the total weight of the modified cellulose solution.

In an aspect, a method of making an aqueous natural binder can comprise a step of contacting at least a portion of the modified cellulose (e.g., modified cellulose solution) with a strengthening agent to form the aqueous natural binder. The aqueous natural binder can be prepared by combining the modified cellulose with the strengthening agent in any suitable order.

In an aspect, a method of making an aqueous natural binder can further comprise contacting the aqueous natural binder with an additive selected from the group consisting of a softening agent, an electrolyte, a pigment color, and combinations thereof. The aqueous natural binder and methods of making and using same are described in more detail in U.S. Provisional Patent Application No. 62/624,377 filed Jan. 31, 2018, and entitled "Modified Cellulose Based Natural Binder for Nonwoven Fabrics," which is incorporated by reference herein in its entirety.

In an aspect, the aqueous natural binder can be used (e.g., applied) on one or both of the outer surfaces of the fiber web to control dusting, as will be discussed in more detail later herein, in addition to strengthening the fiber web. In aspects where it is desirable that the aqueous natural binder be applied only on the outer surface of the substrate (e.g., fiber web), the aqueous natural binder can be lightly sprayed, printed, foamed, or rolled onto the fiber web.

In an aspect where the fiber web is a multi-layer fiber web, the step of contacting the fiber web with the aqueous natural binder can comprise contacting at least a portion of the first outer layer and/or at least a portion of the second outer layer with the aqueous natural binder; for example in a foam bonding process, print bonding process, a spray bonding process, roll bonding process, etc.

In some aspects, the aqueous natural binder can be used (e.g., applied) on both outer surfaces of the fiber web (e.g., first outer layer and second outer layer).

In some aspects where the aqueous natural binder is applied onto the first outer layer, the step of contacting the fiber web with the aqueous natural binder can further comprise applying the aqueous natural binder onto the second outer layer.

In other aspects, the aqueous natural binder can be used (e.g., applied) on only one of the outer surfaces of the fiber web (e.g., first outer layer). In such aspects, the method of making the nonwoven fabric as disclosed herein can exclude contacting both outer surfaces of the fiber web with the aqueous natural binder (e.g., can exclude contacting the second outer layer with the aqueous natural binder). As will be appreciated by one of skill in the art, and with the help of this disclosure, while the aqueous natural binder can be applied only on one or both of the outer layers of the fiber web (e.g., the first outer layer, the second outer layer, or both the first outer layer and the second outer layer), the aqueous natural binder can penetrate into one or more layers adjacent to the layer that the aqueous natural binder is contacted with.

In other aspects where the aqueous natural binder is applied onto the first outer layer, the step of contacting the fiber web with the aqueous natural binder can further exclude applying the aqueous natural binder onto the second outer layer.

In an aspect, the step of contacting the fiber web with the aqueous natural binder can comprise a foam bonding process, wherein air or water is used to dilute the aqueous natural binder and as a mean to carry the binder to the fibers. Diluting the binder with air rather than with water has the advantage that drying is faster and energy cost is reduced remarkably. Binder foam can be generated mechanically and can be stabilized with a stabilizing agent to prevent collapse during application to the fiber web. Foam can be applied so as to remain at the surface of the fiber web or can be made to penetrate all the way through a fiber web cross-section. At least one reciprocating foam spreader is commonly used to distribute the foam across the width of the web/fabric. The excess foam can be removed through the porous portion of the web (e.g., space between fibers), for example via a vacuum extractor located on a side of the fiber web that is opposite to the side of the web where the foam is applied. Generally, foam bonding has more efficiency drying and the ability to control fabric softness. However, adequate foaming and uniform binder distribution can be difficult to achieve.

In an aspect, the step of contacting the fiber web with the aqueous natural binder can comprise a print bonding process. Generally, for print bonding, the fiber web must be dry. The print bonding process applies the aqueous natural binder only in predetermined areas as dictated by the pattern of the printing surfaces. The aqueous natural binder can be transferred to the fiber web via a feed roll and an engraved roll. As the fiber web passes the engraved roll, it is pressed against the surface by a rubber roll, thereby transferring the aqueous natural binder to the fabric in the predetermined areas. The excess of aqueous natural binder can be removed by a doctor blade. The print bonding process is suitable for applying low levels of binder to the surface of the fiber web.

In an aspect, the step of contacting the fiber web with the aqueous natural binder can comprise a spray bonding process, wherein the aqueous natural binder can be sprayed onto the fiber web. The aqueous natural binder can be sprayed onto a moving fiber web in fine droplet form through a system of nozzles. The spray bonding process can be used to make highly porous and bulky products, where the fiber web does not need to pass between nip rollers. Spraying the binder can provide an opportunity for the aqueous natural binder solution to penetrate fibers material beneath the immediate surface of the fiber web being sprayed. The liquid binder (e.g., aqueous natural binder) can be atomized by air pressure, hydraulic pressure, and/or centrifugal force and is generally applied to an upper surface of the fiber web. The depth of penetration of the binder into the substrate depends on a variety of factors such as the wettability of the fibers, permeability of the web, and amount of binder. The spray bonding process can allow for the nonwoven to not be compressed, thereby allowing the nonwoven to substantially retain original bulk and structure. In some aspects, the aqueous natural binder can be sprayed onto a dry fiber web. In other aspects, the aqueous natural binder can be sprayed onto a wet fiber web, such as a pre-wetted web.

In some aspects, the fiber web can be impregnated or saturated with the aqueous natural binder, wherein the aqueous natural binder penetrates the fiber web across its entire thickness (e.g., wherein the aqueous natural binder substantially penetrates all layers of a multi-layer fiber web), for example in a saturation bonding process.

In an aspect, the step of contacting the fiber web with the aqueous natural binder can comprise a saturation bonding process. Saturation chemical bonding involves complete immersion of a nonwoven web (e.g., fiber web) in a bath containing a binder (e.g., aqueous natural binder), followed by the excess binder being removed by a pair of nip rolls (e.g., pinch rolls). The fiber web is guided through a saturation bath by rollers and then is pressed between a pair of nip rolls to squeeze out excess liquid (e.g., aqueous natural binder). The amount of aqueous natural binder taken up by the nonwoven depends on a variety of factors such as the basis weight of the nonwoven, length of time spent in the bath, wettability of the fibers, and nip pressure. The saturation bonding process can provide relatively high binder to fiber levels uniformly throughout the nonwoven. However, the saturation bonding process includes short wetting time, and as such is more suitable for lightweight and highly permeable nonwovens.

In an aspect, the fiber web and the aqueous natural binder can be contacted at a fabric to liquor ratio of from about 1:0.01 to about 1:20, alternatively from about 1:0.02 to about 1:18, alternatively from about 1:0.05 to about 1:15, or alternatively from about 1:0.07 to about 1:10, wherein the fabric to liquor ratio is a mass to volume ratio expressed in kg fiber web to liters of aqueous natural binder. For example, a fabric to liquor ratio of 1:0.01 refers to a ratio of 1 kg of fiber web to 0.01 liters of aqueous natural binder; a fabric to liquor ratio of 1:20 refers to a ratio of 1 kg of fiber web to 20 liters of aqueous cellulosic; etc. For purposes of the disclosure herein the term "liquor" refers to the aqueous natural binder. Further, for purposes of the disclosure herein the term "fabric to liquor ratio" refers to the fabric to aqueous natural binder ratio expressed in kg fiber web to liters of aqueous natural binder.

In an aspect, a method of making a nonwoven fabric as disclosed herein can comprise a step of curing the binder impregnated fiber web to form the nonwoven fabric, wherein the nonwoven fabric comprises a cured natural binder, and wherein the cured natural binder comprises at least a portion of the modified cellulose of the aqueous natural binder and at least a portion of the strengthening agent of the aqueous natural binder.

As used herein, "curing," "cured" and similar terms are intended to encompass the structural and/or morphological change which occurs in a binder composition (e.g., aqueous binder composition) of the present disclosure, such as by covalent chemical reaction (crosslinking), ionic interaction or clustering, improved adhesion to the fiber web substrate, phase transformation or inversion, and hydrogen bonding when the binder composition is dried and heated to cure the binder. As used herein, the term "cured binder" refers to the cured product of the natural binder, which cured product bonds the fibers of a fibrous product (e.g., fiber web) together. Generally, the bonding occurs at an intersection of overlapping fibers.

Figure 1B:
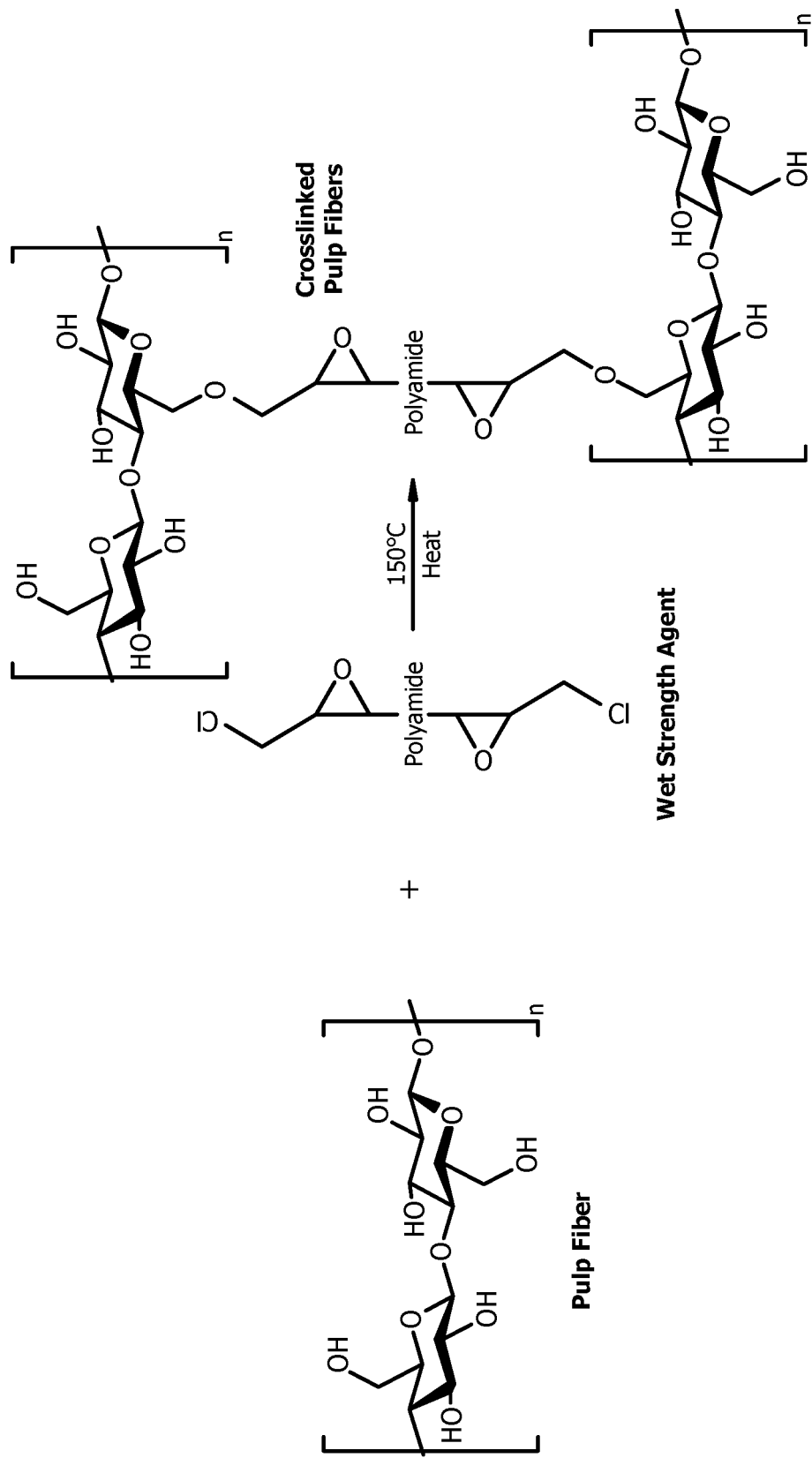

For example, and without wishing to be limited by theory, FIG. 1A displays a proposed crosslinking reaction mechanism between modified cellulose and citric acid (e.g., crosslinking agent) that leads to the formation of covalent bonds between cellulose molecules via citric acid covalent crosslinks. FIG. 1B displays a proposed crosslinking reaction mechanism between modified cellulose and a wet strength agent that leads to the formation of covalent bonds between cellulose molecules via wet strength agent covalent crosslinks. Without wishing to be limited by theory, at dry condition (i.e., subsequent to curing the binder), crosslinking agent and/or wet strength agent can create the covalent/ester bond between cellulose fibers.

In an aspect, the step of curing the binder impregnated fiber web to form the nonwoven fabric can comprise drying the binder impregnated fiber web, for example by heating the binder impregnated fiber web to a temperature of from about 110° C. to about 220° C., alternatively from about 115° C. to about 215° C., alternatively from about 120° C. to about 210° C., alternatively from about 130° C. to about 200° C., or alternatively from about 140° C. to about 170° C. The binder impregnated fiber web can be heated by any suitable methodology.

After the binder is applied, the binder impregnated fiber web can be dried, for example in any suitable dryer or oven, to evaporate the binder carrier (e.g., water) and allow the natural binder to bond the nonwovens, for example via chemical bonding (e.g., covalent bonding via the crosslinking agent, as previously described herein). Nonlimiting examples of dryers suitable for use in the present disclosure include drum dryers, heated drums, steam-heated drying cans, flat belt dryers, stenter-based dryers, thru-air ovens, perforated-drum dryers, infrared dryers, and the like, or combinations thereof. In drum drying or belt drying, the fiber web can be guided over a perforated conveyor surface through which hot air passes, for example air heated to a temperature of from about 110° C. to about 220° C. Air can then be withdrawn from the inside of the drum or through the perforations of the belt and can be reused. Stenter dryers can provide hot air flow to both surfaces of the binder impregnated fiber web. In infrared dryers, water from the binder absorbs infrared energy and it evaporates.

In an aspect, the step of curing the binder impregnated fiber web to form the nonwoven fabric can further comprise thermal bonding. As used herein, the term "thermal bonding" refers to a technique for bonding a web of fibers in which a heat and/or ultrasonic treatment, with or without pressure, is used to activate a heat-sensitive material. The heat-sensitive material can be in the form of fibers, bicomponent fibers and fusable powders, including as part of the web. The bonding may be applied all over (e.g., through bonding or area bonding) or restricted to predetermined, discrete sites (e.g., point bonding). Nonlimiting examples of thermal bonding suitable for use in the present disclosure include calendering, through-air thermal bonding, radiant heat bonding, sonic bonding, and the like, or combinations thereof. Calendering uses heat and high pressure applied through rollers to weld the fiber webs together. Through-air thermal bonding makes bulkier products by the overall bonding of a fiber web containing low melting point fibers, wherein the melting of the fibers takes place in a carefully temperature controlled hot air stream. Drum and blanket systems apply pressure and heat to make products of average bulk. Radiant heat bonding can be achieved by exposing the fiber web to a source of radiant energy in the infrared range, which increases the temperature of the web. Sonic bonding takes place when the molecules of the fibers held under a patterned roller are excited by high frequency energy which produces internal heating.

In an aspect, the fibers of the nonwoven material can be held together by the natural binder; or by the natural binder and melted or partially melted synthetic fibers, such as bicomponent fibers. In some aspects, the fiber web can comprise bicomponent fibers, wherein the bicomponent fibers comprise a core and a sheath surrounding the core. In such aspect, during thermal bonding of the binder impregnated fiber web at least a portion of the sheath can melt during the thermal bonding and can provide for further bonding of the fiber web.

In aspects where the fibers of the nonwoven material are held together by the natural binder, the nonwoven material can be referred to as "natural-bonded nonwoven fabric." In aspects where the fibers of the nonwoven material are held together by the cellulosic type material (e.g., cellulosic fibers, cellulosic binder), the nonwoven material can be referred to as "cellulose-bonded nonwoven fabric."

In aspects where the fibers of the nonwoven material are airlaid and held together by the natural binder, the nonwoven material can be referred to as "natural-bonded airlaid (NBAL) nonwoven fabric." In aspects where the fibers of the nonwoven material are airlaid and held together by the cellulosic type material (e.g., cellulosic fibers, cellulosic binder), the nonwoven material can be referred to as "cellulose-bonded airlaid (CBAL) nonwoven fabric."

In an aspect, the single-layer nonwoven fabric can be a single-layer CBAL nonwoven fabric. In an aspect, the single-layer nonwoven fabric can be a single-layer NBAL nonwoven fabric.

In an aspect, the multi-layer nonwoven fabric can be a multi-layer CBAL nonwoven fabric. In an aspect, the multi-layer nonwoven fabric can be a multi-layer NBAL nonwoven fabric.

In aspects where the step of curing the binder impregnated fiber web to form the nonwoven fabric comprises both thermal bonding and chemical bonding, the nonwoven fabric can be referred to as a "multi-bonded nonwoven fabric." Generally, a multi-bonded nonwoven fabric refers to a nonwoven fabric produced by using two or more different bonding techniques, such as thermal bonding and chemical bonding, for example.

In an aspect, a nonwoven fabric (e.g., single-layer nonwoven fabric, multi-layer nonwoven fabric) can comprise a fiber web (e.g., single-layer fiber web, multi-layer fiber web) as disclosed herein and a cured natural binder as disclosed herein. The fiber web (e.g., single-layer fiber web, multi-layer fiber web) can be present in the nonwoven fabric in an amount of from about 85 wt. % to about 99.99 wt. %, alternatively from about 87 wt. % to about 99.5 wt. %, or alternatively from about 90 wt. % to about 99 wt. %, based on the total weight of the nonwoven fabric. The cured natural binder can be present in the nonwoven fabric in an amount of from about 0.01 wt. % to about 15 wt. %, alternatively from about 0.5 wt. % to about 13 wt. %, or alternatively from about 1 wt. % to about 10 wt. %, based on the total weight of the nonwoven fabric. The nonwoven fabric can comprise natural fibers (e.g., cellulosic fibers) and synthetic fibers in any suitable amount to confer the desired properties to the nonwoven fabric. For purposes of the disclosure herein, the cured natural binder can also be referred to as the "natural binder," and the terms "cured natural binder" and "natural binder" can be used interchangeably.

In some aspects, the natural binder and/or aqueous natural binder can be characterized by a degree of biodegradability of equal to or greater than about 99%, alternatively equal to or greater than about 99.5%, or alternatively equal to or greater than about 99.9%, wherein the degree of biodegradability refers to aerobic biodegradability in soil as determined in accordance with ISO 17556:2003 E. In an aspect, the natural binder and/or aqueous natural binder can be characterized by a degree of biodegradability of 100%, wherein the degree of biodegradability refers to aerobic biodegradability in soil as determined in accordance with ISO 17556:2003 E.

In an aspect, the nonwoven fabric (e.g., single-layer nonwoven fabric, multi-layer nonwoven fabric) as disclosed herein can comprise the cured natural binder in an amount of from about 0.005 $g/m^2$ to about 10 $g/m^2$, alternatively from about 0.01 $g/m^2$ to about 9 $g/m^2$, alternatively from about 0.1 $g/m^2$ to about 8 $g/m^2$, or alternatively from about 1 $g/m^2$ to about 7 $g/m^2$, based on the surface area of the nonwoven fabric.

In an aspect, the amount of cured natural binder in the nonwoven fabric (e.g., single-layer nonwoven fabric, multi-layer nonwoven fabric) can be less than an amount of latex binder in an otherwise similar nonwoven fabric that has been treated with a latex-based binder without modified cellulose.

In an aspect, the amount of binder in the nonwoven fabric (e.g., single-layer nonwoven fabric, multi-layer nonwoven fabric) can be decreased by equal to or greater than about 70%, alternatively equal to or greater than about 75%, or alternatively equal to or greater than about 80%, when compared to an amount of binder in an otherwise similar nonwoven fabric that has been treated with a latex-based binder without modified cellulose.

In an aspect, the cured natural binder as disclosed herein can comprise modified cellulose and strengthening agent in a weight ratio of strengthening agent to modified cellulose of from about 1:2 to about 1:1,000, alternatively from about 1:3 to about 1:750, alternatively from about 1:4 to about 1:500, or alternatively from about 1:5 to about 1:100.

In an aspect, the cured natural binder as disclosed herein can comprise the modified cellulose in an amount of from about 50 wt. % to about 99 wt. %, alternatively from about 55 wt. % to about 94 wt. %, or alternatively from about 60 wt. % to about 89 wt. %, based on the total weight of the cured natural binder.

In an aspect, the cured natural binder as disclosed herein can comprise the strengthening agent in an amount of from about 1 wt. % to about 50 wt. %, alternatively from about 6 wt. % to about 45 wt. %, or alternatively from about 11 wt. % to about 40 wt. %, based on the total weight of the cured natural binder; wherein the strengthening agent can comprise the crosslinking agent and/or the wet strength agent.

In an aspect, the cured natural binder as disclosed herein can comprise the crosslinking agent in an amount of from about 1 wt. % to about 50 wt. %, alternatively from about 6 wt. % to about 45 wt. %, or alternatively from about 11 wt. % to about 40 wt. %, based on the total weight of the cured natural binder.

In an aspect, the cured natural binder as disclosed herein can comprise a wet strength agent in an amount of from about 1 wt. % to about 50 wt. %, alternatively from about 6 wt. % to about 45 wt. %, or alternatively from about 11 wt. % to about 40 wt. %, based on the total weight of the cured natural binder.

In an aspect, the cured natural binder as disclosed herein can further comprise a softening agent in an amount of from about 1 wt. % to about 25 wt. %, alternatively from about 2 wt. % to about 20 wt. %, or alternatively from about 3 wt. % to about 10 wt. %, based on the total weight of the cured natural binder.

In an aspect, the cured natural binder as disclosed herein can further comprise an electrolyte in an amount of from about 0.1 wt. % to about 1 wt. %, alternatively from about 0.2 wt. % to about 0.9 wt. %, or alternatively from about 0.3 wt. % to about 0.8 wt. %, based on the total weight of the cured natural binder.

In an aspect, the nonwoven fabric (e.g., single-layer nonwoven fabric, multi-layer nonwoven fabric) as disclosed herein can exclude latex. In an aspect, the nonwoven fabric (e.g., single-layer nonwoven fabric, multi-layer nonwoven fabric) as disclosed herein can be substantially latex-free. In an aspect, the nonwoven fabric (e.g., single-layer nonwoven fabric, multi-layer nonwoven fabric) as disclosed herein can be essentially latex-free. In an aspect, the nonwoven fabric (e.g., single-layer nonwoven fabric, multi-layer nonwoven fabric) as disclosed herein can comprise 0 wt. % latex, based on the total weight of the nonwoven fabric.

In an aspect, the nonwoven fabric (e.g., single-layer nonwoven fabric, multi-layer nonwoven fabric) as disclosed herein can exclude formaldehyde. In an aspect, the nonwoven fabric (e.g., single-layer nonwoven fabric, multi-layer nonwoven fabric) as disclosed herein can be substantially formaldehyde-free. In an aspect, the nonwoven fabric (e.g., single-layer nonwoven fabric, multi-layer nonwoven fabric) as disclosed herein can be essentially formaldehyde-free. In an aspect, the nonwoven fabric (e.g., single-layer nonwoven fabric, multi-layer nonwoven fabric) as disclosed herein can comprise 0 wt. % formaldehyde, based on the total weight of the nonwoven fabric.

In an aspect, the nonwoven fabric (e.g., multi-layer nonwoven fabric) can comprise natural fibers (e.g., cellulosic fibers) in an amount of from about 50 wt. % to about 99 wt. %, alternatively from about 60 wt. % to about 95 wt. %, alternatively from about 70 wt. % to about 90 wt. %, alternatively from about 75 wt. % to about 85 wt. %, or alternatively from about 77.5 wt. % to about 82.5 wt. %, based on the total weight of the nonwoven fabric.

In an aspect, the nonwoven fabric (e.g., multi-layer nonwoven fabric) can comprise synthetic fibers (e.g., bicomponent fibers) in an amount of from about 1 wt. % to about 50 wt. %, alternatively from about 5 wt. % to about 40 wt. %, alternatively from about 10 wt. % to about 30 wt. %, alternatively from about 15 wt. % to about 25 wt. %, or alternatively from about 17.5 wt. % to about 22.5 wt. %, based on the total weight of the nonwoven fabric.

In an aspect, the amount of synthetic fibers in a nonwoven fabric (e.g., multi-layer nonwoven fabric) cured via both thermal bonding and chemical bonding can be less than an amount of synthetic fibers in an otherwise similar nonwoven fabric that has been cured via thermal bonding without chemical bonding.

In an aspect, the amount of synthetic fibers in the nonwoven fabric (e.g., multi-layer nonwoven fabric) cured via both thermal bonding and chemical bonding can be decreased by equal to or greater than about 25%, alternatively equal to or greater than about 30%, or alternatively equal to or greater than about 35% when compared to an amount of synthetic fibers in an otherwise similar nonwoven fabric that has been cured via thermal bonding without chemical bonding.

In some aspects, the nonwoven fabric (e.g., single-layer nonwoven fabric) can comprise natural fibers (e.g., cellulosic fibers), and no synthetic fibers. In such aspects, the fiber web (e.g., single-layer fiber web) can be present in the nonwoven fabric (e.g., single-layer nonwoven fabric) in an amount of from about 85 wt. % to about 99.99 wt. %, alternatively from about 87 wt. % to about 99.5 wt. %, or alternatively from about 90 wt. % to about 99 wt. %, based on the total weight of the nonwoven fabric. In such aspects, the cured natural binder can be present in the nonwoven fabric (e.g., single-layer nonwoven fabric) in an amount of from about 0.01 wt. % to about 15 wt. %, alternatively from about 0.5 wt. % to about 13 wt. %, or alternatively from about 1 wt. % to about 10 wt. %, based on the total weight of the nonwoven fabric.

In an aspect, the nonwoven fabric (e.g., multi-layer nonwoven fabric) as disclosed herein can include any suitable additive, as dictated by the intended use of the nonwoven fabric. Nonlimiting examples of additives suitable for use in the present disclosure include antimicrobial agents, dyes, opacity enhancers, delustrants, brighteners, skin-care additives, odor control agents, detackifying agents, particulates, preservatives, wetting agents, cleaning agents, detergents, surfactants, silicones, emollients, lubricants, fragrance, fragrance solubilizers, fluorescent whitening agents, UV absorbers, pharmaceuticals, pH control agents, and the like, or combinations thereof.

In an aspect, the nonwoven fabric (e.g., multi-layer nonwoven fabric) can be biodegradable, wherein the fiber web comprises natural fibers (e.g., cellulosic fibers), and biodegradable synthetic fibers (e.g., PLA-based polymers, PBS-based polymers, PLA/PBS fibers). In such aspect, the nonwoven fabric (e.g., multi-layer nonwoven fabric) can further comprise a natural binder.

In an aspect, the nonwoven fabric (e.g., single-layer nonwoven fabric) can be biodegradable, wherein the fiber web comprises natural fibers (e.g., cellulosic fibers, biodegradable cellulosic fibers). In such aspect, the nonwoven fabric (e.g., single-layer nonwoven fabric) can further comprise a natural binder (e.g., biodegradable natural binder). The natural binder (e.g., cured natural binder) can comprise modified cellulose (e.g., biodegradable modified cellulose).

In an aspect, the nonwoven fabric (e.g., multi-layer nonwoven fabric) can be non-biodegradable, wherein the fiber web comprises natural fibers (e.g., cellulosic fibers), and non-biodegradable synthetic fibers (e.g., PET and/or PE fibers). In such aspect, the nonwoven fabric (e.g., multi-layer nonwoven fabric) can further comprise a natural binder.

In aspects where the fiber web comprises biodegradable fibers (e.g., cellulosic fibers, and optionally biodegradable synthetic fibers), the nonwoven fabric can be characterized by a degree of biodegradability of equal to or greater than about 99%, alternatively equal to or greater than about 99.5%, or alternatively equal to or greater than about 99.9%, wherein the degree of biodegradability refers to aerobic biodegradability in soil as determined in accordance with ISO 17556:2003 E. In such aspects, the fiber web can comprise, consist of, or consist essentially of biodegradable fibers, such as biodegradable natural fibers (e.g., cellulosic fibers) and optionally biodegradable synthetic fibers (e.g., PLA-based fibers, PBS-based fibers, PLA/PBS-based fibers). In some aspects, the biodegradable synthetic fibers comprise bicomponent fibers comprising PLA-based polymers and PBS-based polymers (e.g., PLA/PBS bicomponent fibers). In such aspects, the fiber web can exclude non-biodegradable synthetic fibers.

In an aspect, the nonwoven fabric (e.g., multi-layer nonwoven fabric) can be characterized by a degree of biodegradability of 100%, wherein the degree of biodegradability refers to aerobic biodegradability in soil as determined in accordance with ISO 17556:2003 E. In such aspect, the fiber web can comprise, consist of, or consist essentially of biodegradable fibers, such as biodegradable natural fibers (e.g., cellulosic fibers) and biodegradable synthetic fibers (e.g., PLA-based fibers, PBS-based fibers, PLA/PBS-based fibers). In such aspect, the fiber web can exclude non-biodegradable synthetic fibers.

In an aspect, the nonwoven fabric (e.g., single-layer nonwoven fabric) can be characterized by a degree of biodegradability of 100%, wherein the degree of biodegradability refers to aerobic biodegradability in soil as determined in accordance with ISO 17556:2003 E. In such aspect, the fiber web can comprise, consist of, or consist essentially of biodegradable fibers. In such aspect, the fiber web can exclude synthetic fibers.

In aspects where the fiber web (e.g., multi-layer fiber web) comprises non-biodegradable fibers, the nonwoven fabric (e.g., multi-layer nonwoven fabric) can be non-biodegradable. In such aspects, the nonwoven fabric (e.g., multi-layer nonwoven fabric) can further comprise natural fibers (e.g., cellulosic fibers) and a natural binder.

In an aspect, the nonwoven fabric (e.g., multi-layer nonwoven fabric) as disclosed herein can be a multi-layer nonwoven fabric. The multi-layer nonwoven fabric comprises a first outer layer, a second outer layer, and optionally one or more intermediate layers, wherein the one or more intermediate layers are disposed between the first outer layer and the second outer layer. For purposes of the disclosure herein, the first outer layer can also be referred to as the "bottom layer," and the terms "first outer layer" and "bottom layer" can be used interchangeably. Further, for purposes of the disclosure herein, the second outer later can also be referred to as the "top layer," and the terms "second outer layer" and "top layer" can be used interchangeably.

In some aspects, the multi-layer nonwoven fabric has no intermediate layers, i.e., the multi-layer nonwoven fabric is a bi-layer nonwoven fabric comprising the first outer layer and the second outer layer. In other aspects, the multi-layer nonwoven fabric can comprise from 1 to about 10 intermediate layers, alternatively from about 2 to about 9 intermediate layers, or alternatively from about 3 to about 7 intermediate layers.

The layers of the multi-layer nonwoven fabric are substantially parallel to each other, wherein any two adjacent layers are in physical contact with (e.g., touch) each other. For example, the layers of the multi-layer nonwoven fabric are substantially parallel to each other over any 1 μm², alternatively any 100 μm², or alternatively any 1 mm² surface area of the multi-layer nonwoven fabric. As will be appreciated by one of skill in the art, and with the help of this disclosure, while the layers of the multi-layer nonwoven fabric are substantially parallel to each other (e.g., over any 1 μm², alternatively any 100 μm², or alternatively any 1 mm² surface area of the multi-layer nonwoven fabric), the multi-layer nonwoven fabric can have a planar configuration or a non-planar configuration. The multi-layer nonwoven fabric can be a planar sheet, a rolled sheet, a folded sheet, a crimped sheet, etc., wherein the layers of the multi-layer nonwoven fabric are substantially parallel to each other (e.g., over any 1 μm², alternatively any 100 μm², or alternatively any 1 mm² surface area of the multi-layer nonwoven fabric).

For example, the bottom layer and the intermediate layer adjacent to the bottom layer are substantially parallel with each other, wherein the bottom layer is in physical contact with the intermediate layer adjacent to the bottom layer. As another example, the top layer and the intermediate layer adjacent to the top layer are substantially parallel with each other, wherein the top layer is in physical contact with the intermediate layer adjacent to the top layer. As yet another example, an inner intermediate layer is in physical contact with the two intermediate layers adjacent to the inner intermediate layer (e.g., the inner intermediate layer is disposed between the two intermediate layers adjacent to the inner intermediate layer; the inner intermediate layer is sandwiched between the two intermediate layers adjacent to the inner intermediate layer), wherein all three intermediate layers (i.e., inner intermediate layer and the two intermediate layers adjacent to the inner intermediate layer) are substantially parallel with each other.

For purposes of the disclosure herein, the multi-layer nonwoven fabric can be characterized by a fabric thickness, wherein the fabric thickness is the distance from one outer surface (e.g., top or upper surface) of the nonwoven fabric to the other outer surface (e.g., bottom or lower surface) of the nonwoven fabric, across a cross-section of the nonwoven fabric, wherein the cross-section is substantially orthogonal to the layers of the nonwoven fabric. For purposes of the disclosure herein, the fabric thickness can also be referred to as the "caliper," and the terms "fabric thickness" and "caliper" can be used interchangeably. The caliper or thickness of a fabric can be measured under a specified pressure.

In an aspect, the nonwoven fabric (e.g., multi-layer nonwoven fabric) as disclosed herein can be characterized by a caliper of equal to or greater than about 0.1 mm, alternatively equal to or greater than about 0.5 mm, alternatively equal to or greater than about 1 mm, alternatively from about 0.1 mm to about 18 mm, alternatively from about 0.1 mm to about 15 mm, alternatively from about 0.1 mm to about 10 mm, alternatively from about 0.5 mm to about 4 mm, or alternatively from about 0.5 mm to about 2.5 mm, as determined in accordance with EDANA 30.5-99.

In an aspect, the nonwoven fabric (e.g., multi-layer nonwoven fabric) as disclosed herein can be characterized by a caliper which can be increased by equal to or greater than about 10%, alternatively equal to or greater than about 15%, or alternatively equal to or greater than about 20% when compared to a caliper of an otherwise similar nonwoven fabric that has been treated with a latex-based binder without modified cellulose, wherein the caliper is determined in accordance with EDANA 30.5-99.

In an aspect, the first outer layer and/or the second outer layer comprise the cured natural binder. In some aspects, each layer of the multi-layer nonwoven fabric comprises the cured natural binder. In other aspects, the one or more intermediate layers exclude the cured natural binder. In yet other aspects, the second outer layer excludes the cured natural binder.

In some aspects, the first outer layer and the second outer layer comprise the cured natural binder.

In other aspects, the first outer layer comprises the cured natural binder, and the second outer layer excludes the cured natural binder.

As will be appreciated by one of skill in the art, and with the help of this disclosure, the cured natural binder increases the thickness of the nonwoven fabric (e.g., multi-layer nonwoven fabric). Without wishing to be limited by theory, the natural binder can penetrate into the nonwoven fabric (e.g., the natural binder can penetrate into one or more of the layers of the multi-layer nonwoven fabric), and by being present on and/or between the fibers of the fiber web, the natural binder can increase the thickness of the fiber web, and consequently increase the thickness of the nonwoven fabric (e.g., multi-layer nonwoven fabric). Further, and without wishing to be limited by theory, the natural binder can be deposited onto an outer surface of the nonwoven fabric (e.g., the natural binder can coat one or both of the outer layers of the multi-layer nonwoven fabric), thereby increasing the thickness of the nonwoven fabric (e.g., multi-layer nonwoven fabric). For example, if the caliper or thickness of the nonwoven fabric is t, then the cured natural binder coated on one or both of the outer surfaces of the nonwoven fabric can provide for (e.g., account for) equal to or greater than about 5%, alternatively equal to or greater than about 10%, or alternatively equal to or greater than about 25% of t; e.g., the cured natural binder coated on one or both of the outer surfaces of the nonwoven fabric extends from the fibers of the fiber web for equal to or greater than about 5%, alternatively equal to or greater than about 10%, alternatively equal to or greater than about 15%, alternatively equal to or greater than about 20%, alternatively equal to or greater than about 25%, or alternatively equal to or greater than about 30% of t. For example, a fiber web (e.g., multi-layer fiber web) untreated with binder can have a thickness of about 0.9 mm, and a nonwoven fabric (e.g., multi-layer nonwoven fabric) that has been treated with natural binder can have a thickness of about 1.3 mm; wherein the cured natural binder extends from the fibers of the fiber web for about 0.4 mm, which is about 31% of the nonwoven fabric thickness.

The synthetic fibers can be present in each layer of the multi-layer nonwoven fabric in an amount of from about 0 wt. % to about 100 wt. %, alternatively from about 0.5 wt. % to about 50 wt. %, alternatively from about 1 wt. % to about 40 wt. %, or alternatively from about 1 wt. % to about 20 wt. %, based on the total weight of the layer. The natural fibers can be present in each layer of the multi-layer nonwoven fabric in an amount of from about 0 wt. % to about 100 wt. %, alternatively from about 50 wt. % to about 99.5 wt. %, alternatively from about 60 wt. % to about 99 wt. %, or alternatively from about 80 wt. % to about 99 wt. %, based on the total weight of the layer.

In some aspects, at least one layer of the multi-layer nonwoven fabric (i) comprises natural fibers and (ii) excludes synthetic fibers.

In other aspects, at least one layer of the multi-layer nonwoven fabric (iii) comprises synthetic fibers and (iv) excludes natural fibers.

In yet other aspects, each layer of the multi-layer nonwoven fabric comprises natural fibers and synthetic fibers.

In an aspect, the nonwoven fabric (e.g., multi-layer nonwoven fabric) as disclosed herein has a non-uniform concentration of synthetic fibers across a cross-section of the nonwoven fabric (e.g., across t), wherein the layers of the nonwoven fabric are substantially parallel to each other, and wherein the cross-section is substantially orthogonal to the layers of the nonwoven fabric. As will be appreciated by one of skill in the art, and with the help of this disclosure, while the fiber web prior to bonding may have distinguishable layers or strata as previously described herein, subsequent to the bonding process, the multi-layer nonwoven fabric may or may not have layers distinguishable from each other (e.g., for example visually distinguishable, or distinguishable via an optical microscope). However, and for purposes of the disclosure herein, a nonwoven fabric having a non-uniform concentration of synthetic fibers across t can be referred to as a "multi-layer nonwoven fabric," wherein the multi-layer nonwoven fabric may or may not have layers distinguishable from each other. Further, and for purposes of the disclosure herein, in the case of a multi-layer nonwoven fabric that does not have layers distinguishable from each other, a layer of the multi-layer nonwoven fabric can be defined by any suitable cross-section through the fabric substantially parallel to an outer surface of the nonwoven fabric.

In some aspects, the nonwoven fabric (e.g., multi-layer nonwoven fabric) as disclosed herein has a uniform concentration gradient of synthetic fibers across a cross-section of the nonwoven fabric (e.g., along t), wherein the layers of the nonwoven fabric are substantially parallel to each other, and wherein the cross-section is substantially orthogonal to the layers of the nonwoven fabric. For example, the concentration of synthetic fibers can increase or decrease substantially continuously along t. As another example, the concentration of synthetic fibers can increase or decrease step-wise along t. As will be appreciated by one of skill in the art, and with the help of this disclosure, while the concentration of synthetic fibers within any given layer of the multi-layer nonwoven fabric can be substantially constant, the concentration of synthetic fibers can vary continuously from one layer to another, and as such can establish a step-wise uniform concentration gradient of synthetic fibers across a cross-section of the nonwoven fabric. Generally, a concentration gradient refers to the variation in concentration, which can be either uniform (i.e., it varies at a substantially constant rate) or non-uniform (i.e., it varies at a variable rate).

In other aspects, the nonwoven fabric (e.g., multi-layer nonwoven fabric) as disclosed herein has a non-uniform concentration gradient of synthetic fibers across a cross-section of the nonwoven fabric (e.g., along t), wherein the layers of the nonwoven fabric are substantially parallel to each other, and wherein the cross-section is substantially orthogonal to the layers of the nonwoven fabric. For example, the concentration of synthetic fibers can increase along a portion of t (e.g., along one or more layers of the multi-layer nonwoven fabric); the concentration of synthetic fibers can decrease along a portion of t (e.g., along one or more layers of the multi-layer nonwoven fabric); the concentration of synthetic fibers can stay substantially the same along a portion of t (e.g., along one or more layers of the multi-layer nonwoven fabric); or combinations thereof. The increase or decrease in concentration can be continuous or step-wise. The amount of synthetic fibers can be adjusted or varied across t or a portion thereof to provide for a desired synthetic fiber concentration gradient profile.

In an aspect, at least two adjacent layers of the multi-layer nonwoven fabric have different amounts of synthetic fibers as compared to each other.

In some aspects, an amount of natural fibers in the first outer layer is greater than an amount of natural fibers in the second outer layer. In other aspects, an amount of natural fibers in the second outer layer is greater than an amount of natural fibers in the first outer layer. In yet other aspects, an amount of natural fibers in the first outer layer is substantially the same as an amount of natural fibers in the second outer layer.

In an aspect, the synthetic fibers can be present in the first outer layer in an amount of from about 1 wt. % to about 20 wt. %, alternatively from about 5 wt. % to about 17.5 wt. %, or alternatively from about 10 wt. % to about 15 wt. %, based on the total weight of the first outer layer.

In an aspect, the synthetic fibers can be present in the second outer layer in an amount of from about 20 wt. % to about 40 wt. %, alternatively from about 22.5 wt. % to about 35 wt. %, or alternatively from about 25 wt. % to about 30 wt. %, based on the total weight of the second outer layer.

In some aspects, the synthetic fibers are present in each layer of the one or more intermediate layers in an amount of from about 10 wt. % to about 40 wt. %, alternatively from about 12.5 wt. % to about 37.5 wt. %, or alternatively from about 15 wt. % to about 35 wt. %, based on the total weight of the intermediate layer.

In some aspects, an amount of synthetic fibers in the first outer layer is less than an amount of synthetic fibers in any of the intermediate layers. In other aspects, the amount of synthetic fibers in the first outer layer is greater than the amount of synthetic fibers in at least one of the intermediate layers.

In some aspects, an amount of synthetic fibers in at least one of the one or more intermediate layers is less than an amount of synthetic fibers in the second outer layer. In other aspects, an amount of synthetic fibers in at least one of the one or more intermediate layers is greater than an amount of synthetic fibers in the second outer layer.

In an aspect, the nonwoven fabric (e.g., single-layer nonwoven fabric, multi-layer nonwoven fabric) comprising the cured natural binder as disclosed herein can be characterized by enhanced tensile properties, when compared to an otherwise similar nonwoven fabric that has been treated with a latex-based binder without modified cellulose. As will be appreciated by one of skill in the art, and with the help of this disclosure, the tensile properties of the nonwoven fabric depend upon a variety of factors, such as the type of fibers in the web, the method used for forming the web, the type of binder used, the methods used for applying the binder to the web, curing method for the binder, curing time for the binder, etc. Generally, the integrity of the nonwoven fabric can be assessed by tensile testing, for example by dry tensile strength measured in the machine direction (MD), wet tensile strength measured in the cross direction (CD), and the like, or combinations thereof. Typically, the tensile strength for nonwoven fabrics is measured in cross direction wet strength and machine direction dry strength, but can also be measured in cross direction dry strength and machine direction wet strength.

In an aspect, the nonwoven fabric (e.g., single-layer nonwoven fabric, multi-layer nonwoven fabric) as disclosed herein can be characterized by a dry tensile strength measured in the machine direction of equal to or greater than about 670 grams per linear inch (gli), alternatively equal to or greater than about 750 gli, or alternatively equal to or greater than about 1,000 gli, as determined in accordance with EDANA 20.2-89.

In some aspects, the nonwoven fabric (e.g., single-layer nonwoven fabric, multi-layer nonwoven fabric) as disclosed herein can be characterized by a water wet tensile strength measured in the cross direction of equal to or greater than about 315 gli, alternatively equal to or greater than about 400 gli, or alternatively equal to or greater than about 600 gli, as determined in accordance with EDANA 20.2-89. In such aspects, the nonwoven fabric (e.g., single-layer nonwoven fabric, multi-layer nonwoven fabric) can comprise a natural binder comprising a strengthening agent (e.g., wet strength agent, crosslinking agent).

In some aspects, the nonwoven fabric (e.g., single-layer nonwoven fabric, multi-layer nonwoven fabric) as disclosed herein can be characterized by a water wet tensile strength measured in the cross direction which is increased by equal to or greater than about 15%, alternatively equal to or greater than about 20%, or alternatively equal to or greater than about 25%, when compared to a water wet tensile strength measured in the cross direction of an otherwise similar nonwoven fabric that has been treated with a latex-based binder without modified cellulose, and wherein the tensile strength is determined in accordance with EDANA 20.2-89. In such aspects, the nonwoven fabric (e.g., single-layer nonwoven fabric, multi-layer nonwoven fabric) can comprise a natural binder comprising a strengthening agent (e.g., wet strength agent, crosslinking agent).

In other aspects, the nonwoven fabric (e.g., single-layer nonwoven fabric) as disclosed herein can be characterized by a water wet tensile strength measured in the cross direction of less than about 250 gli, alternatively less than about 200 gli, alternatively less than about 150 gli, alternatively less than about 100 gli, or alternatively less than about 50 gli, as determined in accordance with EDANA 20.2-89. In such aspects, the single-layer nonwoven fabric can comprise a natural binder lacking a strengthening agent (e.g., wet strength agent, crosslinking agent). In such aspects, the single-layer nonwoven fabric excludes a wet strength agent.

In an aspect, a single-layer nonwoven fabric comprising a natural binder without a strengthening agent (e.g., wet strength agent, crosslinking agent) can be characterized by a water wet tensile strength measured in the cross direction of less than about 250 gli, alternatively less than about 200 gli, alternatively less than about 150 gli, alternatively less than about 100 gli, or alternatively less than about 50 gli, as determined in accordance with EDANA 20.2-89. In such aspects, the single-layer nonwoven fabric excludes a wet strength agent.

In an aspect, the nonwoven fabric (e.g., single-layer nonwoven fabric) as disclosed herein can be characterized by a water wet tensile strength measured in the cross direction which is decreased by equal to or greater than about 25%, alternatively equal to or greater than about 40%, or alternatively equal to or greater than about 50%, when compared to a water wet tensile strength measured in the cross direction of an otherwise similar nonwoven fabric that has been treated with a natural binder without a strengthening agent (e.g., wet strength agent, crosslinking agent), and wherein the tensile strength is determined in accordance with EDANA 20.2-89.

In an aspect, the single-layer nonwoven fabric as disclosed herein can be characterized by a water wet tensile strength measured in the cross direction which is decreased by equal to or greater than about 25%, alternatively equal to or greater than about 40%, or alternatively equal to or greater than about 50%, when compared to a water wet tensile strength measured in the cross direction of an otherwise similar single-layer nonwoven fabric that has been treated with a natural binder without a wet strength agent, and wherein the tensile strength is determined in accordance with EDANA 20.2-89.

As will be appreciated by one of skill in the art, and with the help of this disclosure, nonwovens with a reduced water wet tensile strength can be characterized by an enhanced dispersibility, which can be a desirable feature in certain nonwoven fabrics. For purposes of the disclosure herein, the term "dispersibility" refers to the physical separation of nonwovens into smaller pieces. In some aspects, nonwovens may be used as a component of a wide variety of absorbent structures, such as surgical flushable nonwovens and/or dispersible nonwovens (flushable wipes, dispersible wipes). In such aspects, it may be desirable for the nonwovens to have an enhanced dispersibility, e.g., a reduced dispersion time. For purposes of the disclosure herein, the term "dispersion time" refers to a measure of dispersibility of nonwovens.

In an aspect, the single-layer nonwoven fabric as disclosed herein can be characterized by a dispersion time in water of less than about 10 seconds, alternatively less than about 5 seconds, or alternatively less than about 1 second, wherein the dispersion time is determined via a slosh box tester in accordance with GD3 INDA/EDANA. In such aspect, the single-layer nonwoven fabric can comprise a natural binder without a strengthening agent (e.g., wet strength agent, crosslinking agent). In such aspects, the single-layer nonwoven fabric excludes a wet strength agent. The dispersion time in water increases with increasing the amount of strengthening agent (e.g., wet strength agent, crosslinking agent) in the natural binder. As will be appreciated by one of skill in the art, and with the help of this disclosure, and without wishing to be limited by theory, an increased amount of strengthening agent (e.g., wet strength agent, crosslinking agent) can lead to an increased number of covalent bonds between the strengthening agent (e.g., wet strength agent, crosslinking agent), and both the modified cellulose in the natural binder and the fiber web (e.g., cellulosic fibers of the fiber web), which in turn delays the breaking down of the nonwoven.

Generally, nonwoven materials can exhibit relatively high dust levels, which is typically difficult to control with conventional binder compositions, such as latex binder compositions. Elevated dust levels can be a health concern, as well as an environmental concern.

In an aspect, the nonwoven fabric (e.g., single-layer nonwoven fabric, multi-layer nonwoven fabric) as disclosed herein can be characterized by a dust level of less than about 12 wt. %, alternatively less than about 10 wt. %, alternatively less than about 7 wt. %, alternatively less than about 5 wt. %, alternatively less than about 4 wt. %, or alternatively less than about 3 wt. %, based on the total weight of the nonwoven fabric. The dust level can be determined by as follows. A nonwoven fabric can be cut in a 11"×8" size sheet and then again cut in strips every ½", parallel to the cross-machine direction; and then the strips can be cut again into ½" lengths. A ½" length nonwoven fabric specimen can be weighed and then placed inside a U.S. Standard Testing Sieve, No. 14. The sieve containing the ½" length nonwoven fabric specimen can be maintained under a vacuum of 30 mm Hg while agitating the nonwoven fabric specimen for about 7 minutes with an agitation nozzle. At the end of the 7 minutes agitation period, the agitation nozzle can be stopped, and the nonwoven fabric specimen can be weighed again. The difference between initial and final weight of nonwoven fabric specimen indicates the dust level of nonwoven fabric.

In some aspects, nonwovens may be used as a component of a wide variety of absorbent structures, such as surgical drapes and associated materials, diapers, feminine hygiene materials, wipes, mops, and the like. In such aspects, it may be desirable for the nonwovens to have an enhanced water absorbency.

In an aspect, the nonwoven fabric (e.g., single-layer nonwoven fabric, multi-layer nonwoven fabric) as disclosed herein can be characterized by a water absorbency of equal to or greater than about 15 grams of water per gram of nonwoven fabric (g/gm), alternatively equal to or greater than about 17.5 g/gm, or alternatively equal to or greater than about 20 g/gm, as determined in accordance with EDANA 10.3-99.

In an aspect, the nonwoven fabric (e.g., single-layer nonwoven fabric, multi-layer nonwoven fabric) as disclosed herein can be characterized by a water absorbency which can be increased by equal to or greater than about 30%, alternatively equal to or greater than about 40%, or alternatively equal to or greater than about 50% when compared to a water absorbency of an otherwise similar nonwoven fabric that has been treated with a latex-based binder without modified cellulose, wherein the water absorbency is determined in accordance with EDANA 10.3-99.

In an aspect, the nonwoven fabric (e.g., single-layer nonwoven fabric, multi-layer nonwoven fabric) as disclosed herein can be characterized by a basis weight of from about 30 $g/m^2$ to about 300 $g/m^2$, alternatively from about 35 $g/m^2$ to about 200 $g/m^2$, alternatively from about 40 $g/m^2$ to about 100 $g/m^2$, alternatively from about 40 $g/m^2$ to about 60 $g/m^2$, alternatively less than about 100 $g/m^2$, alternatively less than about 75 $g/m^2$, alternatively less than about 60 $g/m^2$, or alternatively less than about 50 $g/m^2$, based on the surface area of the nonwoven fabric, wherein the basis weight is determined in accordance with TAPPI/ANSI T 410 om-08.

In an aspect, the nonwoven fabric (e.g., single-layer nonwoven fabric, multi-layer nonwoven fabric) as disclosed herein can be characterized by a basis weight which is decreased by equal to or greater than about 16%, alternatively equal to or greater than about 20%, or alternatively equal to or greater than about 25%, when compared to a basis weight of an otherwise similar nonwoven fabric that has been treated with a latex-based binder without modified cellulose, and wherein the basis weight is determined in accordance with TAPPI/ANSI T 410 om-08. As will be appreciated by one of skill in the art, and with the help of this disclosure, nonwoven fabrics with lower basis weight that can maintain the desired properties are produced by using a lower amount of raw materials, such as fibers and binder, thus resulting in advantageous cost savings.

In an aspect, the nonwoven fabric (e.g., single-layer nonwoven fabric, multi-layer nonwoven fabric) comprising the cured natural binder as disclosed herein can be formed into any suitable article of manufacture by using any suitable methodology. Nonlimiting examples of articles that can be formed from the nonwoven fabrics (e.g., single-layer nonwoven fabric, multi-layer nonwoven fabric) of the present disclosure include wipes, wet wipes, baby wipes, disinfecting wipes, tissues, towels, double re-creped (DRC) items, medical drapes, bandages, caps, face masks, surgical scrubs, medical gowns, filters, diapers, padding, packaging, insulation, carpeting, upholstery, fabric dryer sheets, disposable textiles, earphone protection covers, insulation, wall coverings, seed blankets, agricultural wraps, and the like, or combinations thereof.

In an aspect, a method of making a multi-layer nonwoven fabric as disclosed herein can comprise the steps of (a) forming a plurality of fibers into a multi-layer fiber web via an airlaid process; wherein the multi-layer fiber web comprises a first outer layer, a second outer layer, and optionally one or more intermediate layers, wherein the one or more intermediate layers are disposed between the first outer layer and the second outer layer; wherein each layer of the multi-layer fiber web comprises natural fibers and synthetic fibers; (b) spraying at least a portion of the first outer layer and/or at least a portion of the second outer layer with an aqueous natural binder to font) a binder impregnated fiber web, wherein the aqueous natural binder comprises modified cellulose, a strengthening agent, and water, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof; and (c) curing the binder impregnated fiber web at temperature of from about 110° C. to about 220° C. to form the multi-layer nonwoven fabric; wherein the multi-layer nonwoven fabric comprises the multi-layer fiber web in an amount of from about 85 wt. % to about 99.99 wt. %, based on the total weight of the multi-layer nonwoven fabric; and wherein the multi-layer nonwoven fabric comprises a cured natural binder in an amount of from about 0.01 wt. % to about 15 wt. %, based on the total weight of the multi-layer nonwoven fabric. In such aspect, the multi-layer nonwoven fabric can be a multi-bonded airlaid nonwoven fabric.

In an aspect, a multi-bonded airlaid multi-layer nonwoven fabric as disclosed herein can comprise a fiber web in an amount of from about 85 wt. % to about 99.99 wt. %, based on the total weight of the multi-layer nonwoven fabric; and a cured natural binder in an amount of from about 0.01 wt. % to about 15 wt. %, based on the total weight of the multi-layer nonwoven fabric; wherein the fiber web comprises a first outer layer, a second outer layer, and optionally one or more intermediate layers, wherein the one or more intermediate layers are disposed between the first outer layer and the second outer layer; wherein the first outer layer and/or the second outer layer comprise the cured natural binder; wherein each layer of the fiber web comprises natural fibers and synthetic fibers; wherein the cured natural binder comprises modified cellulose and a strengthening agent, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof; and wherein the cured natural binder is characterized by a weight ratio of strengthening agent to modified cellulose of from about 1:2 to about 1:1,000. In such aspect, the multi-layer nonwoven fabric has a non-uniform concentration gradient of synthetic fibers across a cross-section of the nonwoven fabric, wherein the layers of the nonwoven fabric are substantially parallel to each other, and wherein the cross-section is substantially orthogonal to the layers of the nonwoven fabric. In some aspects, the first outer layer comprises the cured natural binder; wherein the second outer layer excludes the cured natural binder; and wherein an amount of natural fibers in the first outer layer is greater than an amount of natural fibers in the second outer layer.

In an aspect, a multi-bonded airlaid nonwoven fabric (e.g., multi-bonded airlaid multi-layer nonwoven fabric) as disclosed herein can comprise a fiber web in an amount of from about 85 wt. % to about 99.99 wt. %, based on the total weight of the nonwoven fabric; and a cured natural binder in an amount of from about 0.01 wt. % to about 15 wt. %, based on the total weight of the nonwoven fabric; wherein the fiber web comprises natural fibers and non-biodegradable synthetic fibers; wherein the non-biodegradable synthetic fibers can comprise PET and/or PE. In such aspect, the nonwoven fabric (e.g., multi-layer nonwoven fabric) can be non-biodegradable.

In an aspect, a single-layer nonwoven fabric can comprise a fiber web in an amount of from about 85 wt. % to about 99.99 wt. %, based on the total weight of the single-layer nonwoven fabric; and a cured natural binder in an amount of from about 0.01 wt. % to about 15 wt. %, based on the total weight of the single-layer nonwoven fabric; wherein the fiber web comprises natural fibers; wherein the natural fibers are present in the single-layer nonwoven fabric in an amount of from about 85 wt. % to about 99.99 wt. %, based on the total weight of the single-layer nonwoven fabric; wherein the cured natural binder comprises modified cellulose and a strengthening agent in a weight ratio of strengthening agent to modified cellulose of from about 1:2 to about 1:1,000, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof. In such aspect, the single-layer nonwoven fabric can be a single-layer CBAL nonwoven fabric. In such aspect, the single-layer nonwoven fabric can be a single-layer NBAL nonwoven fabric. In such aspect, the single-layer nonwoven fabric can be biodegradable.

In an aspect, the nonwoven fabrics (e.g., single-layer nonwoven fabrics, multi-layer nonwoven fabrics) and methods of making and using same as disclosed herein can advantageously display improvements in one or more composition characteristics when compared to conventional nonwoven fabrics employing latex binders and methods of making and using same, respectively. About a million tons conventional latex binders are often applied into nonwoven fabric annually. In conventional nonwoven fabric manufacturing processes, about 15% to 26% latex binder is required to achieve the desired properties of nonwoven fabric. Conventional latex binders are fairly expensive (about $3,000/MT) and can contribute to environmental concerns. The natural binders as disclosed herein are much cheaper than latex binders, and can be applied in significantly lower amounts (about 1% to 2%), thereby resulting in a huge manufacturing cost savings. Additionally, large volumes of latex binder are required to achieve the minimum quality target for nonwovens, leading to the use of latex-based binders being more costly.

In an aspect, the environmental impact of reducing or eliminating the use of latex-based binders can be advantageous, as emissions linked to the volatile byproducts of the latex binder can pose environmental and health concerns.

In an aspect, the natural binder as disclosed herein is a natural binder that is advantageously both biodegradable and formaldehyde-free (e.g., environmentally friendly).

In an aspect, the nonwoven fabrics (e.g., single-layer nonwoven fabrics, multi-layer nonwoven fabrics) as disclosed herein can advantageously comprise a decreased amount of binder, when compared to the amount of binder used in conventional nonwoven fabrics employing latex binders. In such aspect, the natural binder treated nonwovens can display reduced environmental and health concerns as compared to latex binder-treated nonwoven fabrics.

In an aspect, the natural binder as disclosed herein is a natural product, which can advantageously exclude latex, acrylamide, formaldehyde, and other synthetic ingredients commonly used in conventional synthetic latex binders. The modified cellulose (e.g., CMC and/or sodium CMC) and the crosslinking agent (e.g., citric acid) are natural-based products, minimally modified. The natural binder as disclosed herein can be advantageously made from food grade ingredients, such as CMC and/or sodium CMC, citric acid, as well as a softening agent, which can be polyethylene glycol, a compound used for human consumption to alleviate constipation. Further, the synthetic fibers can be naturally-derived, such as PLA-based fibers, PBS-based fibers, or PLA/PBS-based fibers. The use of natural-based ingredients in the nonwoven fabrics (e.g., single-layer nonwoven fabrics, multi-layer nonwoven fabrics) as disclosed herein can advantageously allow for the nonwoven fabrics to be biodegradable.

In an aspect, the nonwoven fabrics (e.g., single-layer nonwoven fabrics, multi-layer nonwoven fabrics) as disclosed herein can advantageously display increased strength and decreased dust levels when compared to nonwovens comprising conventional latex-based binders. An improvement in dust level can reduce the environmental and health hazard impact of the nonwoven manufacturing process. As will be appreciated by one of skill in the art, and with the help of this disclosure, conventional nonwoven fabrics are generally characterized by high dust levels, a concern in nonwovens manufacturing.

In an aspect, the nonwoven fabrics (e.g., multi-layer nonwoven fabrics) as disclosed herein can be advantageously designed with desired amounts of synthetic fibers in each layer in order to confer desired properties (e.g., tensile strength, dust level, caliper, etc.) to the nonwovens.

In some aspects, the top layer of the nonwoven fabrics (e.g., multi-layer nonwoven fabrics) as disclosed herein can display an embossed pattern, for example in the case of baby wipes that can have any suitable pattern designs, such as flowers, ducks, toys, etc.

In an aspect, the use of two or more different bonding techniques in a multi-bonded nonwoven fabric (e.g., multi-layer nonwoven fabric) can advantageously decrease the amount of synthetic fibers that is used in the nonwoven fabric. Additional advantages the nonwoven fabrics (e.g., single-layer nonwoven fabrics, multi-layer nonwoven fabrics) and methods of making and using same as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner. All composition % are wt. %, unless otherwise specified herein.

Example 1

Natural binder compositions were prepared and used as follows. Modified cellulose (e.g., CMC and/or sodium CMC) was dissolved in water to produce a modified cellulose solution. Citric acid and polyethylene glycol were added to the modified cellulose solution to form the aqueous natural binder compositions. 1 liter of natural binder was prepared by using 30 g CMC, 15 g citric acid, 15 g polyethylene glycol, and 950 g of water. The modified cellulose, citric acid, and polyethylene glycol were dissolved in water separately, to yield the modified cellulose solution, citric acid solution, and polyethylene glycol solution, respectively. Further, both the citric acid solution and the polyethylene glycol solution were blended into the modified cellulose solution, and then the blended product was stirred for 30 minutes at room temperature to form the aqueous natural binder composition.

Example 2

Natural binder compositions were prepared and used as follows. Modified cellulose (e.g., CMC and/or sodium CMC) was dissolved in water to produce a modified cellulose solution. A wet strength agent and polyethylene emulsion solutions were added to the modified cellulose solution to form the aqueous natural binder compositions. The wet strength agent was POLYCUP crosslinking resin. 1 liter of natural binder was prepared by using 30 g CMC, 3.6 g wet strength agent, 10 g polyethylene emulsion, and 956.4 g of water. The modified cellulose, wet strength agent and polyethylene emulsion were mixed in water separately, to yield the modified cellulose solution, wet strength agent solution, and polyethylene emulsion solution, respectively. Further, both the wet strength agent solution, and polyethylene emulsion solution were blended into the modified cellulose solution, and then the blended product was stirred for 30 minutes at room temperature to form the aqueous natural binder composition.

Nonwovens were produced with a hand sheet molding machine, as well as with a production machine.

Hand sheets (nonwoven fabric) were prepared with a hand sheet molding machine, and the hand sheets were subjected to testing to determine properties such as tensile strength properties, absorbency, caliper, and dust level. Each natural binder sample was sprayed on the surface of the fiber web with a spray machine.

The basis weight target for latex-free multi-bonded airlaid (MBAL) nonwovens was same as the basis weigh target for thermal-bonded airlaid (TBAL) nonwovens, at 50 gsm. The amount of bicomponent fiber used for the latex-free MBAL nonwoven was the same as for conventional MBAL nonwoven at 20 wt. %, based on the total weight of the nonwoven.

Figure 2:
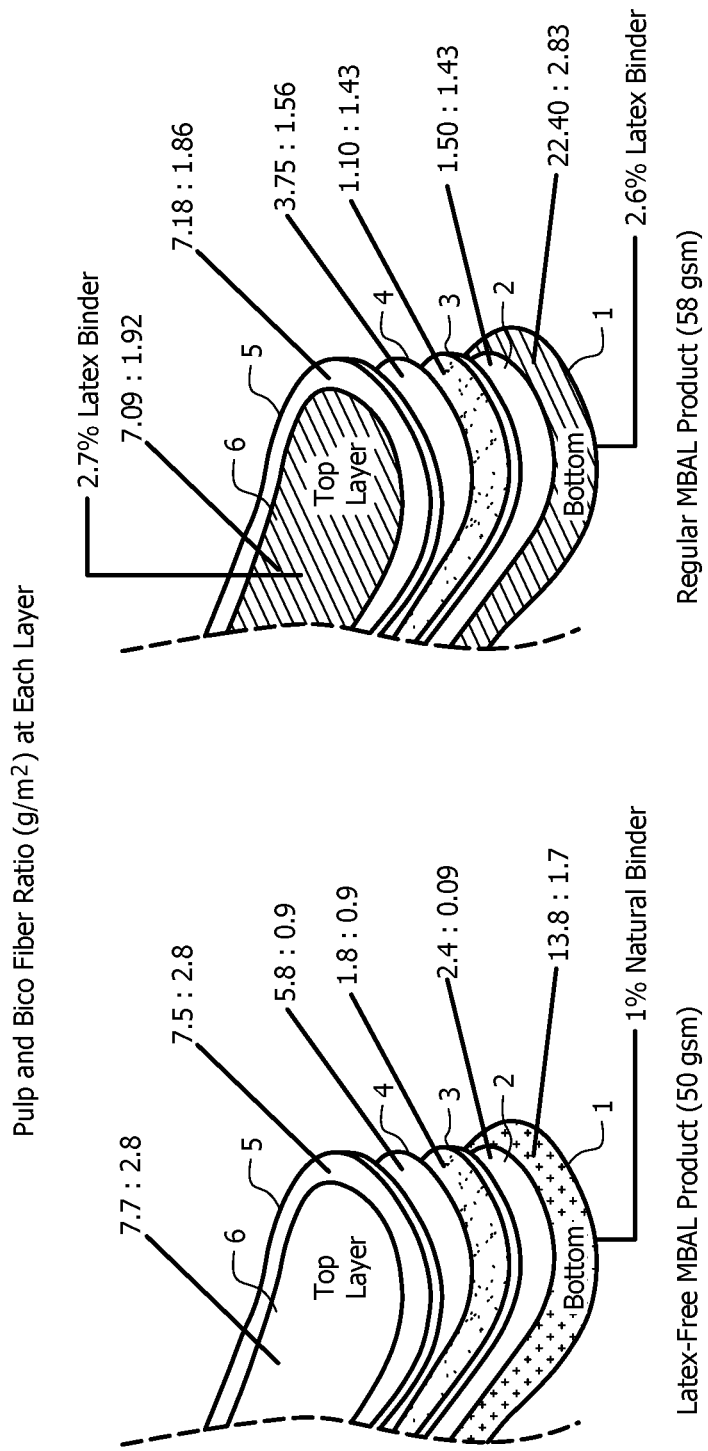
FIG. 2 displays a schematic of a multi-layer nonwoven fabric.

The latex-free MBAL nonwoven (e.g., multi-layer nonwoven fabric as disclosed herein) was produced with six layers: two outer layers, and 4 intermediate layers, as displayed in FIG. 2. The raw materials composition of the first outer layer (layer #1 or bottom layer) was 88.2 wt. % wood pulp and 11.8 wt. % bicomponent fiber (13.8 $g/m^2$ and 1.8 $g/m^2$, respectively), based on the total weight of the layer; the composition of layer #2 (intermediate layer) was 50.9 wt. % wood pulp and 25.5 wt. % bicomponent fiber (2.4 $g/m^2$ and 0.9 $g/m^2$, respectively), based on the total weight of the layer; the composition of layer #3 (intermediate layer) was 65.7 wt. % wood pulp and 34.3 wt. % bicomponent fiber (1.8 $g/m^2$ and 0.9 $g/m^2$, respectively), based on the total weight of the layer; the composition of layer #4 (intermediate layer) was 86.3 wt. % wood pulp and 13.7 wt. % bicomponent fiber (5.8 $g/m^2$ and 0.9 $g/m^2$, respectively), based on the total weight of the layer; the composition of layer #5 (intermediate layer) was 72.8 wt. % wood pulp and 27.2 wt. % bicomponent fiber (7.5 $g/m^2$ and 2.8 $g/m^2$, respectively), based on the total weight of the layer; and the composition of the second outer layer (layer #6 or top layer)

was 73.2 wt. % wood pulp and 26.8 wt. % bicomponent fiber (7.7 g/m² and 2.8 g/m², respectively), based on the total weight of the layer.

Once the multi-layer fiber web was formed, about 1 wt. % (based on the total weight of the nonwoven) CMC-based natural binder (wherein the binder contained citric acid) was sprayed on the first outer layer (layer #1 or bottom layer) and then the binder impregnated web was cured at 150° C. for 5 minutes for the hand sheet. In addition, about 2% CMC-based natural binder (wherein the binder contained wet strength agent) was also sprayed onto both outer layers and then cured at 150° C. for 5 minutes for the hand sheet. For the production machine, the binder treated fabric was run at 220° C. inside a machine dryer at a speed of 180 meters/min.

Tables 1 and 2 display the physical properties of hand sheet nonwovens and machine trial nonwovens, respectively.

TABLE 1

| Product Name | Raw Materials Composition | | | | Basis Weight (g/m²) | Caliper (mm) | Tensile CD Wet (gli) | Tensile MD Dry (gli) | Absorbency (g/gm) |
|---|---|---|---|---|---|---|---|---|---|
| | Pulp % | Bico % | Latex % | NB % | | | | | |
| Conventional MBAL (control) | 74.0 | 20.0 | 6.0 | 0.0 | 58 | 1.1 | 380 | 716 | 11.0 |
| Latex-free MBAL (Binder sprayed on 1st outer layer only) | 79.0 | 20.0 | 0.0 | 1.0 | 50 | 1.3 | 440 | 700 | 14.5 |
| Latex-free MBAL (Binder sprayed on 1st outer layer only) | 79.0 | 20 | 0.0 | 1.0 | 50 | 1.0 | 530 | 986 | 14.0 |
| Latex-free MBAL (Binder sprayed on both outer layers) | 80 | 18 | 0.0 | 2 | 53 | 1.0 | 800 | 1582 | 13.5 |
| Conventional TBAL (control) | 69.0 | 31.0 | 0.0 | 0.0 | 50 | 1.0 | 410 | 720 | 11.5 |

MD = machine direction;
CD = cross direction

TABLE 2

| Product Name | Basis Weight (g/m²) | Dry Caliper (mm) | Wet Caliper (mm) | Tensile CD Wet (gli) | Elongation (CD Wet) | Tensile MD Dry (gli) | Absorbency (g/gm) | Dust % |
|---|---|---|---|---|---|---|---|---|
| Conventional MBAL (control) | 58 | 1.1 | 0.84 | 387 | 22 | 790 | 11.0 | 9.0 |
| Latex-free MBAL | 50 | 1.1 | 0.62 | 315 | 13 | 670 | 15.0 | 9.5 |
| Latex-free MBAL | 58 | 1.2 | 0.9 | 380 | 10 | 941 | 14.0 | 7.2 |
| Conventional TBAL (control) | 50 | 1.0 | 0.57 | 346 | 15 | 710 | 12.0 | 15.0 |

MD = machine direction;
CD = cross direction

It was observed from Table 1 that CD wet strength of latex-free MBAL hand sheet was significantly higher than that of conventional MBAL and TBAL, but the MD dry strength was about the same. Additionally, when the natural binder contained about 2% wet strength agent, and the natural binder was sprayed onto both outer layers in hand sheet, the CD wet strength and the MD dry strength of hand sheet were increased significantly, wherein the CD wet strength and the MD dry strength of hand sheet were almost twice the corresponding values for conventional MBAL (latex binder) and TBAL hand sheets. It was further observed from Table 2 that CD wet strength and MD dry strength of latex-free MBAL machine trial nonwoven was little bit lower than conventional MBAL and TBAL nonwovens; however, the tensile strength was under-requirement range (specification). Further, the latex-free MBAL nonwoven composition can be adjusted (e.g., by adjusting the amounts of bicomponent fiber and/or natural binder) as desired to full fill the target of tensile strength and other physical properties.

The latex-free MBAL nonwoven can be used as a substitute for the TBAL nonwoven. The latex-free MBAL nonwoven contains 20 wt. % bicomponent fiber and 79 wt. % pulp fiber based on the total weight of the nonwoven, while the TBAL nonwoven contains 31 wt. % bicomponent fiber and 69 wt. % pulp fiber based on the total weight of the nonwoven. As will be appreciated by one of skill in the art, and with the help of this disclosure, the bicomponent fiber is the most expensive raw material in the nonwoven production, with the cost of bicomponent fiber being about four times higher than the cost of pulp fiber. The latex-free MBAL nonwoven contains about 35 wt. % less bicomponent fiber than the TBAL nonwoven, which in turn can advantageously provide for cost savings owing to using less bicomponent fiber.

Further, conventional MBAL nonwoven contains about 6 wt. % latex binder, 20 wt. % bicomponent fiber, and 74 wt. % pulp fiber, based on the total weight of the nonwoven. However, the latex binder can create environmental and health issues due to latex volatiles emission, as well as formaldehyde content, and the latex-free MBAL nonwoven can overcome these potential issues. Additionally, about 16 wt. % raw material can also be saved, since the latex-free MBAL nonwoven basis weight was 50 gsm, as compared to the basis weight of the conventional MBAL nonwoven which was 58 gsm.

Example 3

Natural binder compositions were prepared and used as follows. Modified cellulose (e.g., CMC and/or sodium CMC) was dissolved in water to produce a modified cellulose solution. A wet strength agent was added to the modified cellulose solution to form the aqueous natural binder compositions. The wet strength agent was POLYCUP 2000 crosslinking resin. 1,000 kg of natural binder was prepared by using 30 kg CMC (solid), 4.5 kg wet strength agent (solid), and 965.5 kg of water. The modified cellulose and wet strength agent were mixed in water separately, to yield the modified cellulose solution, and wet strength agent solution, respectively. Further, the wet strength agent solution was blended into the modified cellulose solution, and then the blended product was stirred for 30 minutes at room temperature to form the aqueous natural binder composition.

Nonwovens were produced with a hand sheet molding machine, as well as with a production machine, as described in Example 2.

The biodegradability of the nonwovens was investigated for each of the hand sheet products, as well as for each of the machine trial nonwovens (obtained with the production machine), and the data are displayed in Tables 3 and 4. Tables 3 and 4 display the physical properties and biodegradability of hand sheet nonwovens and machine trial nonwovens, respectively. The nonwovens in Table 3 were MBAL sheet products, wherein the raw materials used for the nonwovens were bicomponent (PLA/PBS) fiber, pulp fiber (e.g., cellulosic fiber), and natural binder. The nonwovens in Table 4 were CBAL machine trial nonwoven fabrics.

TABLE 3

| Product Type (Hand Sheet Product) | Raw Materials Composition | | | | Basis Weight (g/m2) | Caliper (mm) | Tensile CD Wet (gli) | Tensile MD Dry (gli) | Absorbency (g/gm) | Biodegradable |
|---|---|---|---|---|---|---|---|---|---|---|
| | Pulp % | Bico % | Latex % | NB % | | | | | | |
| MBAL | 80.0 | 18 | 0.0 | 2.0 | 58 | 1.0 | 380 | 850 | 13.5 | Yes |
| MBAL | 79.0 | 18 | 0.0 | 3.0 | 58 | 1.0 | 475 | 1110 | 14.0 | Yes |
| MBAL Comparison-control) | 75.0 | 19.0 | 6.0 | 0.0 | 58 | 1.0 | 480 | 1020 | 11.0 | No |

TABLE 4

| Product Type (Machine Product) | Basis weight (gm) | Natural Binder Add on % | Natural Binder with Wet Strength Agent add on % | Caliper (mm) | MD Dry Strength (gli) | CD Wet Strength (gli) | Water Absorption Capacity (g/gm) | Biodegradable |
|---|---|---|---|---|---|---|---|---|
| CBAL | 60 | 2.5 | 0.0 | 0.6 | 1020 | 25 | 11.0 | Yes |
| CBAL | 60 | 3.0 | 0.0 | 0.6 | 1120 | 29 | 11.8 | Yes |
| CBAL | 60 | 3.5 | 0.0 | 0.6 | 1190 | 27 | 11.0 | Yes |
| CBAL | 55 | 0.0 | 2.5 | 0.6 | 1435 | 280 | 11.0 | Yes |
| CBAL | 55 | 0.0 | 3.0 | 0.6 | 1480 | 319 | 10.5 | Yes |

TABLE 4-continued

| Product Type (Machine Product) | Basis weight (gm) | Natural Binder Add on % | Natural Binder with Wet Strength Agent add on % | Caliper (mm) | MD Dry Strength (gli) | CD Wet Strength (gli) | Water Absorption Capacity (g/gm) | Biodegradable |
|---|---|---|---|---|---|---|---|---|
| CBAL | 55 | 0.0 | 3.5 | 0.6 | 1502 | 350 | 11.2 | Yes |
| LBAL with 12% latex binder-6803) (Comparison | 55 | 0.0 | 0.0 | 0.6 | 710 | 303 | 8.2 | No |

As it can be seen from the data in Table 4, the single-layer CBAL machine trial nonwoven fabrics are biodegradable, owing to comprising biodegradable components. When latex was used as a binder in the control LBAL nonwoven fabric, the biodegradability test was negative.

Further, and as it can be seen from the data in Table 4, the single-layer CBAL machine trial nonwoven fabrics obtained without the use of a wet strength agent have a fairly low CD wet strength, below 30 gli, which is an indication that the single-layer CBAL machine trial nonwoven fabrics obtained without the use of a wet strength agent are dispersible, which further indicates that they could be used as dispersible or flushable wipes.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

ADDITIONAL DISCLOSURE

A first aspect, which is a nonwoven fabric comprising a fiber web in an amount of from about 85 wt. % to about 99.99 wt. %, based on the total weight of the nonwoven fabric; and a cured natural binder in an amount of from about 0.01 wt. % to about 15 wt. %, based on the total weight of the nonwoven fabric; wherein the fiber web comprises natural fibers and synthetic fibers; wherein the natural fibers are present in the nonwoven fabric in an amount of from about 70 wt. % to about 90 wt. %, based on the total weight of the nonwoven fabric; wherein the synthetic fibers are present in the nonwoven fabric in an amount of from about 10 wt. % to about 30 wt. %, based on the total weight of the nonwoven fabric; wherein the cured natural binder comprises modified cellulose and a strengthening agent in a weight ratio of strengthening agent to modified cellulose of from about 1:2 to about 1:1,000, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof.

A second aspect, which is the nonwoven fabric of the first aspect, wherein the nonwoven fabric excludes latex.

A third aspect, which is the nonwoven fabric of any one of the first and the second aspects, wherein the nonwoven fabric excludes formaldehyde.

A fourth aspect, which is the nonwoven fabric of any one of the first through the third aspects, wherein the synthetic fibers comprise monocomponent fibers, bicomponent fibers, multicomponent fibers, or combinations thereof.

A fifth aspect, which is the nonwoven fabric of the fourth aspect, wherein the bicomponent fibers have a partially drawn core.

A sixth aspect, which is the nonwoven fabric of any one of the first through the fifth aspects, wherein the natural fibers comprise cellulosic fibers, modified cellulosic fibers, chemically treated cellulosic fibers, chemi-thermally treated cellulosic fibers, mechanically treated cellulosic fibers, thermo-mechanically treated cellulosic fibers, or combinations thereof.

A seventh aspect, which is the nonwoven fabric of any one of the first through the sixth aspects, wherein the carboxylic acid having two or more carboxyl groups comprises citric acid, oxalic acid, malonic acid, succinic acid, glutaric acid, adipic acid, malic acid, polyacrylic acid, or combinations thereof.

An eighth aspect, which is the nonwoven fabric of any one of the first through the seventh aspects, wherein the wet strength agent comprises N-methylolacrylamide (NMA), polyacrylamide (PAM), glyoxylated polyacrylamide (GPAM), polyamide epichlorohydrin (PAE), polyamidoamine epichlorohydrin (PAAE), or combinations thereof.

A ninth aspect, which is the nonwoven fabric of any one of the first through the eighth aspects, wherein the nonwoven fabric is a multi-layer nonwoven fabric.

A tenth aspect, which is the nonwoven fabric of the ninth aspect, wherein the synthetic fibers are present in each layer of the multi-layer nonwoven fabric in an amount of from about 0 wt. % to about 100 wt. %, based on the total weight of the layer.

An eleventh aspect, which is the nonwoven fabric of any one of the first through the tenth aspects, wherein the natural fibers are present in each layer of the multi-layer nonwoven fabric in an amount of from about 0 wt. % to about 100 wt. %, based on the total weight of the layer.

A twelfth aspect, which is the nonwoven fabric of any one of the first through the eleventh aspects, wherein at least one layer of the multi-layer nonwoven fabric (i) comprises natural fibers and (ii) excludes synthetic fibers; and/or wherein at least one layer of the multi-layer nonwoven fabric (iii) comprises synthetic fibers and (iv) excludes natural fibers.

A thirteenth aspect, which is the nonwoven fabric of any one of the first through the twelfth aspects, wherein each layer of the multi-layer nonwoven fabric comprises natural fibers and synthetic fibers.

A fourteenth aspect, which is the nonwoven fabric of any one of the first through the thirteenth aspects, wherein the multi-layer nonwoven fabric comprises a first outer layer, a second outer layer, and optionally one or more intermediate layers, wherein the one or more intermediate layers are disposed between the first outer layer and the second outer layer.

A fifteenth aspect, which is the nonwoven fabric of the fourteenth aspect, wherein the first outer layer and/or the second outer layer comprise the cured natural binder.

A sixteenth aspect, which is the nonwoven fabric of any one of the first through the fifteenth aspects, wherein the first outer layer comprises the cured natural binder.

A seventeenth aspect, which is the nonwoven fabric of the sixteenth aspect, wherein the second outer layer excludes the cured natural binder.

An eighteenth aspect, which is the nonwoven fabric of any one of the first through the sixteenth aspects, wherein the first outer layer and the second outer layer comprise the cured natural binder.

A nineteenth aspect, which is the nonwoven fabric of any one of the first through the eighteenth aspects, wherein an amount of natural fibers in the first outer layer is greater than an amount of natural fibers in the second outer layer.

A twentieth aspect, which is the nonwoven fabric of the nineteenth aspect, wherein the synthetic fibers are present in the first outer layer in an amount of from about 1 wt. % to about 20 wt. %, based on the total weight of the first outer layer; and wherein the synthetic fibers are present in the second outer layer in an amount of from about 20 wt. % to about 40 wt. %, based on the total weight of the second outer layer.

A twenty-first aspect, which is the nonwoven fabric of the twentieth aspect, wherein the synthetic fibers are present in each layer of the one or more intermediate layers in an amount of from about 10 wt. % to about 40 wt. %, based on the total weight of the intermediate layer.

A twenty-second aspect, which is the nonwoven fabric of any one of the first through the twenty-first aspects, wherein an amount of synthetic fibers in the first outer layer is less than an amount of synthetic fibers in the second outer layer, and wherein the amount of synthetic fibers in the first outer layer is less than an amount of synthetic fibers in any of the intermediate layers.

A twenty-third aspect, which is the nonwoven fabric of any one of the first through the twenty-second aspects, wherein an amount of synthetic fibers in at least one of the one or more intermediate layers is less than an amount of synthetic fibers in the second outer layer.

A twenty-fourth aspect, which is the nonwoven fabric of any one of the first through the twenty-third aspects, wherein at least two adjacent layers of the multi-layer nonwoven fabric have different amounts of synthetic fibers as compared to each other.

A twenty-fifth aspect, which is the nonwoven fabric of any one of the first through the twenty-fourth aspects, wherein the multi-layer nonwoven fabric has a non-uniform concentration gradient of synthetic fibers across a cross-section of the nonwoven fabric, wherein the layers of the nonwoven fabric are substantially parallel to each other, and wherein the cross-section is substantially orthogonal to the layers of the nonwoven fabric.

A twenty-sixth aspect, which is the nonwoven fabric of any one of the first through the twenty-fifth aspects, wherein the nonwoven fabric comprises the cured natural binder in an amount of from about 0.005 $g/m^2$ to about 10 $g/m^2$, based on the surface area of the nonwoven fabric.

A twenty-seventh aspect, which is the nonwoven fabric of any one of the first through the twenty-sixth aspects, wherein the nonwoven fabric is a multi-bonded nonwoven fabric.

A twenty-eighth aspect, which is the nonwoven fabric of any one of the first through the twenty-seventh aspects, wherein the nonwoven fabric is an airlaid nonwoven fabric.

A twenty-ninth aspect, which is the nonwoven fabric of any one of the first through the twenty-eighth aspects, wherein the nonwoven fabric is characterized by a dry tensile strength measured in the machine direction of equal to or greater than about 670 grams per linear inch (gli), as determined in accordance with EDANA 20.2-89.

A thirtieth aspect, which is the nonwoven fabric of any one of the first through the twenty-ninth aspects, wherein the nonwoven fabric is characterized by a water wet tensile strength measured in the cross direction of equal to or greater than about 315 grams per linear inch (gli), as determined in accordance with EDANA 20.2-89.

A thirty-first aspect, which is the nonwoven fabric of any one of the first through the thirtieth aspects, wherein the nonwoven fabric is characterized by a water wet tensile strength measured in the cross direction which is increased by equal to or greater than about 15% when compared to a water wet tensile strength measured in the cross direction of an otherwise similar nonwoven fabric that has been treated with a latex-based binder without modified cellulose, and wherein the tensile strength is determined in accordance with EDANA 20.2-89.

A thirty-second aspect, which is the nonwoven fabric of any one of the first through the thirty-first aspects, wherein the nonwoven fabric is characterized by a dust level of less than about 10 wt. %, based on the total weight of the nonwoven fabric.

A thirty-third aspect, which is the nonwoven fabric of any one of the first through the thirty-second aspects, wherein the nonwoven fabric is characterized by a caliper of equal to or greater than about 0.1 mm, as determined in accordance with EDANA 30.5-99.

A thirty-fourth aspect, which is the nonwoven fabric of any one of the first through the thirty-third aspects, wherein the nonwoven fabric is characterized by a caliper which is increased by equal to or greater than about 10% when compared to a caliper of an otherwise similar nonwoven fabric that has been treated with a latex-based binder without modified cellulose, as determined in accordance with EDANA 30.5-99.

A thirty-fifth aspect, which is the nonwoven fabric of any one of the first through the thirty-fourth aspects, wherein the nonwoven fabric is characterized by a water absorbency of equal to or greater than about 15 grams of water per gram of nonwoven fabric (g/gm), as determined in accordance with EDANA 10.3-99.

A thirty-sixth aspect, which is the nonwoven fabric of any one of the first through the thirty-fifth aspects, wherein the nonwoven fabric is characterized by a water absorbency which is increased by equal to or greater than about 30% when compared to a water absorbency of an otherwise similar nonwoven fabric that has been treated with a latex-based binder without modified cellulose, and wherein the water absorbency is determined in accordance with EDANA 10.3-99.

A thirty-seventh aspect, which is the nonwoven fabric of any one of the first through the thirty-sixth aspects, wherein the nonwoven fabric is characterized by a basis weight of from about 30 g/m$^2$ to about 300 g/m$^2$, based on the surface area of the nonwoven fabric, wherein the basis weight is determined in accordance with TAPPI/ANSI T 410 om-08.

A thirty-eighth aspect, which is the nonwoven fabric of any one of the first through the thirty-seventh aspects, wherein the nonwoven fabric is characterized by a basis weight which is decreased by equal to or greater than about 16% when compared to a basis weight of an otherwise similar nonwoven fabric that has been treated with a latex-based binder without modified cellulose, and wherein the basis weight is determined in accordance with TAPPI/ANSI T 410 om-08.

A thirty-ninth aspect, which is the nonwoven fabric of any one of the first through the thirty-eighth aspects, wherein the amount of cured natural binder in the nonwoven fabric is less than an amount of latex binder in an otherwise similar nonwoven fabric that has been treated with a latex-based binder without modified cellulose.

A fortieth aspect, which is the nonwoven fabric of any one of the first through the thirty-ninth aspects, wherein the amount of binder in the nonwoven fabric is decreased by equal to or greater than about 70% when compared to an amount of binder in an otherwise similar nonwoven fabric that has been treated with a latex-based binder without modified cellulose.

A forty-first aspect, which is the nonwoven fabric of any one of the first through the fortieth aspects, wherein the natural fibers comprise cellulosic fibers, wherein the synthetic fibers comprise naturally-derived fibers, and wherein the nonwoven fabric is biodegradable.

A forty-second aspect, which is the nonwoven fabric of any one of the first through the forty-first aspects, wherein the natural fibers comprise cellulosic fibers, wherein the synthetic fibers comprise biodegradable synthetic fibers, and wherein the nonwoven fabric is characterized by a degree of biodegradability of equal to or greater than about 99%, wherein the degree of biodegradability refers to aerobic biodegradability in soil as determined in accordance with ISO 17556:2003 E.

A forty-third aspect, which is the nonwoven fabric of the forty-second aspect, wherein the biodegradable synthetic fibers comprise PLA-based polymers, PBS-based polymers, derivatives thereof, or combinations thereof.

A forty-fourth aspect, which is the nonwoven fabric of the forty-third aspect, wherein the biodegradable synthetic fibers are bicomponent fibers comprising PLA-based polymers and PBS-based polymers.

A forty-fifth aspect, which is the nonwoven fabric of any one of the first through the fortieth aspects, wherein the synthetic fibers comprise polyethylene terephthalate (PET), polyethylene (PE), or combinations thereof; and wherein the nonwoven fabric is non-biodegradable.

A forty-sixth aspect, which is the nonwoven fabric of the forty-fifth aspect, wherein the nonwoven fabric excludes latex.

A forty-seventh aspect, which is the nonwoven fabric of any one of the forty-fifth and the forty-sixth aspects, wherein the nonwoven fabric is a multi-bonded airlaid nonwoven fabric.

A forty-eighth aspect, which is an article formed from the nonwoven fabric of any one of the first through the forty-seventh aspects.

A forty-ninth aspect, which is the article of the forty-eighth aspect, wherein the article is selected from the group consisting of wipes, wet wipes, baby wipes, disinfecting wipes, tissues, towels, double re-creped (DRC) items, medical drapes, bandages, caps, face masks, surgical scrubs, medical gowns, filters, diapers, padding, packaging, insulation, carpeting, upholstery, fabric dryer sheets, disposable textiles, earphone protection covers, insulation, wall coverings, seed blankets, agricultural wraps, and combinations thereof.

A fiftieth aspect, which is a multi-layer nonwoven fabric comprising a fiber web in an amount of from about 85 wt. % to about 99.99 wt. %, based on the total weight of the multi-layer nonwoven fabric; and a cured natural binder in an amount of from about 0.01 wt. % to about 15 wt. %, based on the total weight of the multi-layer nonwoven fabric; wherein the fiber web comprises a first outer layer, a second outer layer, and optionally one or more intermediate layers, wherein the one or more intermediate layers are disposed between the first outer layer and the second outer layer; wherein the first outer layer, the second outer layer, or both the first outer layer and the second outer layer comprise the cured natural binder; wherein each layer of the fiber web comprises natural fibers and synthetic fibers; wherein the cured natural binder comprises modified cellulose and a strengthening agent, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof.

A fifty-first aspect, which is the multi-layer nonwoven fabric of the fiftieth aspect, wherein the natural fibers are present in the multi-layer nonwoven fabric in an amount of from about 70 wt. % to about 90 wt. %, based on the total weight of the multi-layer nonwoven fabric.

A fifty-second aspect, which is the multi-layer nonwoven fabric of the fiftieth aspect, wherein the synthetic fibers are present in the multi-layer nonwoven fabric in an amount of from about 1 wt. % to about 50 wt. %, based on the total weight of the multi-layer nonwoven fabric.

A fifty-third aspect, which is the multi-layer nonwoven fabric of the fifty-second aspect, wherein the synthetic fibers are present in the multi-layer nonwoven fabric in an amount of from about 10 wt. % to about 30 wt. %, based on the total weight of the multi-layer nonwoven fabric.

A fifty-fourth aspect, which is the multi-layer nonwoven fabric of any one of the fiftieth through the fifty-third aspects, wherein an amount of synthetic fibers in at least one of the one or more intermediate layers is less than an amount of synthetic fibers in the first outer layer and/or an amount of synthetic fibers in the second outer layer.

A fifty-fifth aspect, which is the multi-layer nonwoven fabric of any one of the fiftieth through the fifty-third aspects, wherein an amount of synthetic fibers in at least one of the one or more intermediate layers is equal to or greater than an amount of synthetic fibers in the first outer layer and/or an amount of synthetic fibers in the second outer layer.

A fifty-sixth aspect, which is the multi-layer nonwoven fabric of any one of the fiftieth through the fifty-fifth aspects, wherein the multi-layer nonwoven fabric has a non-uniform concentration gradient of synthetic fibers across a cross-section of the nonwoven fabric, wherein the layers of the nonwoven fabric are substantially parallel to each other, and wherein the cross-section is substantially orthogonal to the layers of the nonwoven fabric.

A fifty-seventh aspect, which is the multi-layer nonwoven fabric of any one of the fiftieth through the fifty-sixth aspects, wherein the first outer layer comprises the cured natural binder; wherein the second outer layer excludes the cured natural binder; and wherein an amount of natural fibers in the first outer layer is greater than an amount of natural fibers in the second outer layer.

A fifty-eighth aspect, which is the multi-layer nonwoven fabric of any one of the fiftieth through the fifty-seventh aspects, wherein the multi-layer nonwoven fabric has from 1 to about 10 intermediate layers.

A fifty-ninth aspect, which is the multi-layer nonwoven fabric of any one of the fiftieth through the fifty-eighth aspects, wherein the multi-layer nonwoven fabric is a multi-bonded airlaid nonwoven fabric.

A sixtieth aspect, which is the multi-layer nonwoven fabric of any one of the fiftieth through the fifty-ninth aspects, wherein the cured natural binder is characterized by a weight ratio of strengthening agent to modified cellulose of from about 1:2 to about 1:1,000.

A sixty-first aspect, which is the multi-layer nonwoven fabric of any one of the fiftieth through the sixtieth aspects, wherein the amount of binder in the multi-layer nonwoven fabric is decreased by equal to or greater than about 75% when compared to an amount of binder in an otherwise similar multi-layer nonwoven fabric that has been treated with a latex-based binder without modified cellulose.

A sixty-second aspect, which is the multi-layer nonwoven fabric of any one of the fiftieth through the sixty-first aspects, wherein the multi-layer nonwoven fabric is characterized by a basis weight which is decreased by equal to or greater than about 16% when compared to a basis weight of an otherwise similar multi-layer nonwoven fabric that has been treated with a latex-based binder without modified cellulose, and wherein the basis weight is determined in accordance with TAPPI/ANSI T 410 om-08.

A sixty-third aspect, which is a method of making a nonwoven fabric, the method comprising (a) forming a plurality of fibers into a fiber web; wherein the fiber web comprises natural fibers and synthetic fibers; wherein the natural fibers are present in the fiber web in an amount of from about 70 wt. % to about 90 wt. %, based on the total weight of the fiber web; and wherein the synthetic fibers are present in the fiber web in an amount of from about 10 wt. % to about 30 wt. %, based on the total weight of the fiber web; (b) contacting at least a portion of the fiber web with an aqueous natural binder to form a binder impregnated fiber web, wherein the aqueous natural binder comprises modified cellulose, a strengthening agent, and water, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof; and (c) curing the binder impregnated fiber web to form the nonwoven fabric; wherein the nonwoven fabric comprises the fiber web in an amount of from about 85 wt. % to about 99.99 wt. %, based on the total weight of the nonwoven fabric; and wherein the nonwoven fabric comprises a cured natural binder in an amount of from about 0.01 wt. % to about 15 wt. %, based on the total weight of the nonwoven fabric.

A sixty-fourth aspect, which is the method of the sixty-third aspect, wherein the nonwoven fabric is a multi-layer nonwoven fabric.

A sixty-fifth aspect, which is the method of any one of the sixty-third and the sixty-fourth aspects, wherein the fiber web comprises a first outer layer, a second outer layer, and optionally one or more intermediate layers, wherein the one or more intermediate layers are disposed between the first outer layer and the second outer layer.

A sixty-sixth aspect, which is the method of the sixty-fifth aspect, wherein step (b) comprises contacting at least a portion of the first outer layer and/or at least a portion of the second outer layer with the aqueous natural binder.

A sixty-seventh aspect, which is the method of any one of the sixty-third through the sixty-sixth aspects, wherein an amount of natural fibers in the first outer layer is greater than an amount of natural fibers in the second outer layer, and wherein step (b) comprises contacting at least a portion of the first outer layer with the aqueous natural binder.

A sixty-eighth aspect, which is the method of the sixty-seventh aspect further excluding contacting the second outer layer with the aqueous natural binder.

A sixty-ninth aspect, which is the method of any one of the sixty-third through the sixty-eighth aspects, wherein the cured natural binder comprises at least a portion of the modified cellulose of the aqueous natural binder and at least a portion of the strengthening agent of the aqueous natural binder.

A seventieth aspect, which is the method of any one of the sixty-third through the sixty-ninth aspects, wherein the aqueous natural binder is a sprayable aqueous solution.

A seventy-first aspect, which is the method of the seventieth aspect, wherein step (b) comprises spraying the aqueous natural binder onto the fiber web.

A seventy-second aspect, which is the method of any one of the sixty-third through the seventy-first aspects, wherein the fiber web and the aqueous natural binder are contacted at a fabric to liquor ratio of from about 1:0.01 to about 1:20, wherein the fabric to liquor ratio is a mass to volume ratio expressed in kg fiber web to liters of aqueous natural binder.

A seventy-third aspect, which is the method of any one of the sixty-third through the seventy-second aspects, wherein the aqueous natural binder is characterized by a weight ratio of water to modified cellulose of from about 99.9:0.1 to about 1,000:500.

A seventy-fourth aspect, which is the method of any one of the sixty-third through the seventy-third aspects, wherein the aqueous natural binder is characterized by a weight ratio of strengthening agent to modified cellulose of from about 1:2 to about 1:1,000.

A seventy-fifth aspect, which is the method of any one of the sixty-third through the seventy-fourth aspects, wherein the aqueous natural binder comprises the modified cellulose in an amount of from about 0.1 wt. % to about 50 wt. %, based on the total weight of the aqueous natural binder.

A seventy-sixth aspect, which is the method of any one of the sixty-third through the seventy-fifth aspects, wherein the aqueous natural binder comprises the strengthening agent in an amount of from about 0.1 wt. % to about 10 wt. %, based on the total weight of the aqueous natural binder.

A seventy-seventh aspect, which is the method of any one of the sixty-third through the seventy-sixth aspects, wherein the aqueous natural binder comprises a wet strength agent in an amount of from about 0.01 wt. % to about 10 wt. %, based on the total weight of the aqueous natural binder; and wherein the wet strength agent comprises N-methylolacrylamide (NMA), polyacrylamide (PAM), glyoxylated polyacrylamide (GPAM), polyamide epichlorohydrin (PAE), polyamidoamine epichlorohydrin (PAAE), or combinations thereof.

A seventy-eighth aspect, which is the method of any one of the sixty-third through the seventy-seventh aspects, wherein the aqueous natural binder further comprises a softening agent in an amount of from about 0.01 wt. % to about 10 wt. %, based on the total weight of the aqueous natural binder; and wherein the softening agent comprises an anionic surfactant, glycerol, a polyethylene emulsion, ethylene glycol, polyethylene glycol, propylene glycol, polypropylene glycol, a fatty alcohol ethoxylate, sodium lauryl sulfate, a silicone-based softener, a nanomaterials-based softener, or combinations thereof.

A seventy-ninth aspect, which is the method of any one of the sixty-third through the seventy-eighth aspects, wherein the aqueous natural binder further comprises an electrolyte in an amount of from about 0.1 wt. % to about 1 wt. %, based on the total weight of the aqueous natural binder; and wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof.

An eightieth aspect, which is the method of any one of the sixty-third through the seventy-ninth aspects, wherein step (a) comprises a dry laid process.

An eighty-first aspect, which is the method of the eightieth aspect, wherein the dry laid process comprises an airlaid process.

An eighty-second aspect, which is the method of any one of the sixty-third through the seventy-ninth aspects, wherein step (a) comprises a process selected from the group consisting of an airlaid process, a spunlaid process, and a wet laid process.

An eighty-third aspect, which is the method of any one of the sixty-third through the eighty-second aspects, wherein step (c) comprises heating the binder impregnated fiber web to a temperature of from about 110° C. to about 220° C.

An eighty-fourth aspect, which is the method of any one of the sixty-third through the eighty-third aspects, wherein step (c) comprises thermal bonding and chemical bonding.

An eighty-fifth aspect, which is the method of the eighty-fourth aspect, wherein the synthetic fibers comprise bicomponent fibers, wherein the bicomponent fibers comprise a core and a sheath surrounding the core, and wherein at least a portion of the sheath melts during the thermal bonding and provides for further bonding of the fiber web.

An eighty-sixth aspect, which is the method of any one of the sixty-third through the eighty-fifth aspects, wherein the thermal bonding comprises calendering, through-air thermal bonding, radiant heat bonding, sonic bonding, or combinations thereof.

An eighty-seventh aspect, which is the method of any one of the sixty-third through the eighty-sixth aspects, wherein at least a portion of the carboxylic acid having two or more carboxyl groups forms chemical bonds with the natural fibers and/or the modified cellulose.

An eighty-eighth aspect, which is the method of the eighty-seventh aspect, wherein the chemical bonds comprise covalent bonds and/or ionic bonds.

An eighty-ninth aspect, which is the method of any one of the sixty-third through the eighty-eighth aspects, wherein the aqueous natural binder comprises a wet strength agent, and wherein the wet strength agent chemically bonds to the fiber web.

A ninetieth aspect, which is the method of any one of the sixty-third through the eighty-ninth aspects, wherein the amount of synthetic fibers in the nonwoven fabric cured via both thermal bonding and chemical bonding is less than an amount of synthetic fibers in an otherwise similar nonwoven fabric that has been cured via thermal bonding without chemical bonding.

A ninety-first aspect, which is the method of any one of the sixty-third through the ninetieth aspects, wherein the amount of synthetic fibers in the nonwoven fabric cured via both thermal bonding and chemical bonding is decreased by equal to or greater than about 25% when compared to an amount of synthetic fibers in an otherwise similar nonwoven fabric that has been cured via thermal bonding without chemical bonding.

A ninety-second aspect, which is a method of making a multi-layer nonwoven fabric, the method comprising (a) forming a plurality of fibers into a multi-layer fiber web via a dry laid process; wherein the multi-layer fiber web comprises a first outer layer, a second outer layer, and optionally one or more intermediate layers, wherein the one or more intermediate layers are disposed between the first outer layer and the second outer layer; wherein each layer of the multi-layer fiber web comprises natural fibers and synthetic fibers; (b) contacting at least a portion of the first outer layer and/or at least a portion of the second outer layer with an aqueous natural binder to form a binder impregnated fiber web, wherein the aqueous natural binder comprises modified cellulose, a strengthening agent, and water, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof; and (c) curing the binder impregnated fiber web to form the multi-layer nonwoven fabric; wherein the multi-layer nonwoven fabric comprises the multi-layer fiber web in an amount of from about 85 wt. % to about 99.99 wt. %, based on the total weight of the multi-layer nonwoven fabric; and wherein the multi-layer nonwoven fabric comprises a cured natural binder in an amount of from about 0.01 wt. % to about 15 wt. %, based on the total weight of the multi-layer nonwoven fabric.

A ninety-third aspect, which is the method of the ninety-second aspect, wherein the natural fibers comprise cellulosic fibers, and wherein the natural fibers are present in the multi-layer nonwoven fabric in an amount of from about 70 wt. % to about 90 wt. %, based on the total weight of the multi-layer nonwoven fabric.

A ninety-fourth aspect, which is the method of the ninety-third aspect, wherein the natural fibers are present in the multi-layer nonwoven fabric in an amount of from about 75 wt. % to about 85 wt. %, based on the total weight of the multi-layer nonwoven fabric.

A ninety-fifth aspect, which is the method of any one of the ninety-second through the ninety-fourth aspects, wherein the synthetic fibers comprise bicomponent fibers, and wherein the synthetic fibers are present in the multi-layer nonwoven fabric in an amount of from about 10 wt. % to about 30 wt. %, based on the total weight of the multi-layer nonwoven fabric.

A ninety-sixth aspect, which is the method of any one of the ninety-second through the ninety-fifth aspects, wherein the synthetic fibers are present in the multi-layer nonwoven fabric in an amount of from about 15 wt. % to about 25 wt. %, based on the total weight of the multi-layer nonwoven fabric.

A ninety-seventh aspect, which is the method of any one of the ninety-second through the ninety-sixth aspects, wherein an amount of natural fibers in the first outer layer is greater than an amount of natural fibers in the second outer layer, and wherein step (b) comprises spraying the aqueous natural binder onto the first outer layer.

A ninety-eighth aspect, which is the method of any one of the ninety-second through the ninety-seventh aspects further excluding spraying the aqueous natural binder onto the second outer layer.

A ninety-ninth aspect, which is the method of any one of the ninety-second through the ninety-eighth aspects, wherein the dry laid process comprises an airlaid process.

A hundredth aspect, which is a multi-layer nonwoven fabric comprising a fiber web in an amount of about 98 wt. %, based on the total weight of the multi-layer nonwoven fabric; and a cured natural binder in an amount of about 2 wt. %, based on the total weight of the multi-layer nonwoven fabric; wherein the fiber web comprises a first outer layer, a second outer layer, and optionally one or more intermediate layers, wherein the one or more intermediate layers are disposed between the first outer layer and the second outer layer; wherein the first outer layer, the second outer layer, or both the first outer layer and the second outer layer comprise the cured natural binder; wherein each layer of the fiber web comprises natural fibers and synthetic fibers; wherein the natural fibers are present in the nonwoven fabric in an amount of about 80 wt. %, based on the total weight of the nonwoven fabric; wherein the synthetic fibers are present in the nonwoven fabric in an amount of about 18 wt. %, based on the total weight of the nonwoven fabric; wherein the cured natural binder comprises modified cellulose and a strengthening agent, wherein the cured natural binder is characterized by a weight ratio of strengthening agent to modified cellulose of from about 1:2 to about 1:1,000, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof.

A hundred-and-first aspect, which is the multi-layer nonwoven fabric of the hundredth aspect, wherein both the first outer layer and the second outer layer comprise the cured natural binder.

A hundred-and-second aspect, which is the multi-layer nonwoven fabric of any one of the hundredth and the hundred-and-first aspects, wherein the synthetic fibers comprise bicomponent fibers.

A hundred-and-third aspect, which is a single-layer nonwoven fabric comprising a fiber web in an amount of from about 85 wt. % to about 99.99 wt. %, based on the total weight of the single-layer nonwoven fabric; and a cured natural binder in an amount of from about 0.01 wt. % to about 15 wt. %, based on the total weight of the single-layer nonwoven fabric; wherein the fiber web comprises natural fibers; wherein the natural fibers are present in the single-layer nonwoven fabric in an amount of from about 85 wt. % to about 99.99 wt. %, based on the total weight of the single-layer nonwoven fabric; wherein the cured natural binder comprises modified cellulose and a strengthening agent in a weight ratio of strengthening agent to modified cellulose of from about 1:2 to about 1:1,000, wherein the modified cellulose comprises CMC and/or sodium CMC, wherein the strengthening agent comprises a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof.

A hundred-and-fourth aspect, which is the single-layer nonwoven fabric of the hundred-and-third aspect, wherein the single-layer nonwoven fabric excludes latex.

A hundred-and-fifth aspect, which is the single-layer nonwoven fabric of any one of the hundred-and-third and the hundred-and-fourth aspects, wherein the nonwoven fabric excludes formaldehyde.

A hundred-and-sixth aspect, which is the single-layer nonwoven fabric of any one of the hundred-and-third through the hundred-and-fifth aspects, wherein the natural fibers comprise cellulosic fibers, modified cellulosic fibers, chemically treated cellulosic fibers, chemi-thermally treated cellulosic fibers, mechanically treated cellulosic fibers, thermo-mechanically treated cellulosic fibers, or combinations thereof.

A hundred-and-seventh aspect, which is the single-layer nonwoven fabric of any one of the hundred-and-third through the hundred-and-sixth aspects, wherein the carboxylic acid having two or more carboxyl groups comprises citric acid, oxalic acid, malonic acid, succinic acid, glutaric acid, adipic acid, malic acid, polyacrylic acid, or combinations thereof.

A hundred-and-eighth aspect, which is the single-layer nonwoven fabric of any one of the hundred-and-third through the hundred-and-seventh aspects, wherein the wet strength agent comprises N-methylolacrylamide (NMA), polyacrylamide (PAM), glyoxylated polyacrylamide (GPAM), polyamide epichlorohydrin (PAE), polyamidoamine epichlorohydrin (PAAE), or combinations thereof.

A hundred-and-ninth aspect, which is the single-layer nonwoven fabric of any one of the hundred-and-third through the hundred-and-eighth aspects, wherein the single-layer nonwoven fabric is a CBAL nonwoven fabric.

A hundred-and-tenth aspect, which is the single-layer nonwoven fabric of any one of the hundred-and-third through the hundred-and-ninth aspects, wherein the single-layer nonwoven fabric is a NBAL nonwoven fabric.

A hundred-and-eleventh aspect, which is the single-layer nonwoven fabric of any one of the hundred-and-third through the hundred-and-tenth aspects, wherein the natural fibers comprise cellulosic fibers, and wherein the single-layer nonwoven fabric is biodegradable.

A hundred-and-twelfth aspect, which is the single-layer nonwoven fabric of any one of the hundred-and-third through the hundred-and-eleventh aspects, wherein the natural fibers comprise biodegradable cellulosic fibers, wherein the cured natural binder comprises biodegradable modified cellulose, and wherein the nonwoven fabric is characterized by a degree of biodegradability of equal to or greater than about 99%, wherein the degree of biodegradability refers to aerobic biodegradability in soil as determined in accordance with ISO 17556:2003 E.

A hundred-and-thirteenth aspect, which is an article formed from the single-layer nonwoven fabric of any one of the hundred-and-third through the hundred-and-twelfth aspects, wherein the article is selected from the group consisting of wipes, wet wipes, baby wipes, disinfecting wipes, flushable wipes, dispersible wipes, tissues, towels, double re-creped (DRC) items, medical drapes, bandages, caps, face masks, surgical scrubs, medical gowns, filters, diapers, padding, packaging, insulation, carpeting, upholstery, fabric dryer sheets, disposable textiles, earphone protection covers, insulation, wall coverings, seed blankets, agricultural wraps, and combinations thereof.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A nonwoven fabric comprising a fiber web in an amount of from about 85 wt. % to about 99.99 wt. %, based on the total weight of the nonwoven fabric; and a cured natural binder in an amount of from about 0.01 wt. % to about 15 wt. %, based on the total weight of the nonwoven fabric; wherein the fiber web comprises natural fibers and synthetic fibers; wherein the natural fibers are present in the nonwoven fabric in an amount of from about 70 wt. % to about 90 wt. %, based on the total weight of the nonwoven fabric; wherein the synthetic fibers are present in the nonwoven fabric in an amount of from about 10 wt. % to about 30 wt. %, based on the total weight of the nonwoven fabric; wherein the cured natural binder comprises modified cellulose and a strengthening agent in a weight ratio of strengthening agent to modified cellulose of from about 1:2 to about 1:1,000, wherein the modified cellulose comprises carboxymethylcellulose (CMC) and/or sodium carboxymethylcellulose (sodium CMC), wherein the strengthening agent comprises a crosslinking agent and a wet strength agent, wherein the crosslinking agent comprises a carboxylic acid having two or more carboxyl groups, wherein the wet strength agent comprises at least one reactive functional group selected from the group consisting of a halide group, a chloride group, a fluoride group, a hydroxyl group, and combinations thereof, wherein the natural fibers comprise cellulose fibers, wherein the synthetic fibers comprise biodegradable synthetic fibers, and wherein the nonwoven fabric is characterized by a degree of biodegradability of equal to or greater than about 99%, wherein the degree of biodegradability refers to aerobic biodegradability in soil as determined in accordance with ISO 17556:2003 E, and wherein the nonwoven fabric excludes latex and formaldehyde.

2. The nonwoven fabric of claim 1, wherein the crosslinking agent comprises citric acid.

3. The nonwoven fabric of claim 1, wherein the wet strength agent comprises polyamide epichlorohydrin.

4. The nonwoven fabric of claim 1, wherein the nonwoven fabric comprises the cured natural binder in an amount of from about 0.005 g/m$^2$ to about 10 g/m$^2$, based on the surface area of the nonwoven fabric.

5. The nonwoven fabric of claim 1, wherein the nonwoven fabric is incorporated in an article selected from the group consisting of wipes, wet wipes, baby wipes, disinfecting wipes, tissues, towels, double re-creped (DRC) items, medical drapes, bandages, caps, face masks, surgical scrubs, medical gowns, filters, diapers, padding, packaging, insulation, carpeting, upholstery, fabric dryer sheets, disposable textiles, earphone protection covers, insulation, wall coverings, seed blankets, agricultural wraps, and combinations thereof.

6. A multi-layer nonwoven fabric comprising a fiber web in an amount of from about 85 wt. % to about 99.99 wt. %, based on the total weight of the multi-layer nonwoven fabric; and a cured natural binder in an amount of from about 0.01 wt. % to about 15 wt. %, based on the total weight of the multi-layer nonwoven fabric; wherein the fiber web comprises a first outer layer, a second outer layer, and optionally one or more intermediate layers, wherein the one or more intermediate layers are disposed between the first outer layer and the second outer layer; wherein the first outer layer, the second outer layer, or both the first outer layer and the second outer layer comprise the cured natural binder; wherein each layer of the fiber web comprises natural fibers and synthetic fibers; wherein the cured natural binder comprises modified cellulose and a strengthening agent, wherein the modified cellulose comprises CMC and/or sodium CMC, wherein the strengthening agent comprises a crosslinking agent and a wet strength agent, wherein the crosslinking agent comprises a carboxylic acid having two or more carboxyl groups, wherein the wet strength agent comprises at least one reactive functional group selected from the group consisting of a halide group, a chloride group, a fluoride group, a hydroxyl group, and combinations thereof, wherein the natural fibers comprise cellulose fibers, wherein the synthetic fibers comprise biodegradable synthetic fibers, and wherein the nonwoven fabric is characterized by a degree of biodegradability of equal to or greater than about 99%, wherein the degree of biodegradability refers to aerobic biodegradability in soil as determined in accordance with ISO 17556:2003 E, and wherein the nonwoven fabric excludes latex and formaldehyde.

7. The multi-layer nonwoven fabric of claim 6, wherein the first outer layer comprises the cured natural binder; wherein the second outer layer excludes the cured natural binder; and wherein an amount of natural fibers in the first outer layer is greater than an amount of natural fibers in the second outer layer.

8. A method of making a nonwoven fabric, the method comprising:
 (a) forming a plurality of fibers into a fiber web; wherein the fiber web comprises natural fibers and synthetic fibers; wherein the natural fibers are present in the fiber web in an amount of from about 70 wt. % to about 90 wt. %, based on the total weight of the fiber web; and wherein the synthetic fibers are present in the fiber web in an amount of from about 10 wt. % to about 30 wt. %, based on the total weight of the fiber web;
 (b) contacting at least a portion of the fiber web with an aqueous natural binder to form a binder impregnated fiber web, wherein the aqueous natural binder comprises modified cellulose, a strengthening agent, and water, wherein the modified cellulose comprises CMC and/or sodium CMC, wherein the strengthening agent comprises a crosslinking agent and a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof; and
 (c) curing the binder impregnated fiber web to form the nonwoven fabric; wherein the nonwoven fabric comprises the fiber web in an amount of from about 85 wt. % to about 99.99 wt. %, based on the total weight of the nonwoven fabric; and wherein the nonwoven fabric comprises a cured natural binder in an amount of from about 0.01 wt. % to about 15 wt. %, based on the total weight of the nonwoven fabric,
 wherein the natural fibers comprise cellulose fibers, wherein the synthetic fibers comprise biodegradable synthetic fibers, and wherein the nonwoven fabric is characterized by a degree of biodegradability of equal to or greater than about 99%, wherein the degree of biodegradability refers to aerobic biodegradability in soil as determined in accordance with ISO 17556:2003 E, and wherein the nonwoven fabric excludes latex and formaldehyde.

9. The method of claim 8, wherein step (a) comprises a process selected from the group consisting of an airlaid process, a spunlaid process, and a wet laid process.

10. The method of claim 8, wherein step (c) comprises heating the binder impregnated fiber web to a temperature of from about 110° C. to about 220° C.

11. The method of claim 8, wherein step (c) comprises thermal bonding and chemical bonding.

12. The method of claim 8, wherein the nonwoven fabric comprises a multi-layer nonwoven fabric, wherein the forming the fiber web comprises forming the plurality of fibers into a multi-layer fiber web via a dry laid process,
 wherein the multi-layer fiber web comprises a first outer layer, a second outer layer, and optionally one or more intermediate layers, wherein the one or more intermediate layers are disposed between the first outer layer and the second outer layer; wherein each layer of the multi-layer fiber web comprises natural fibers and synthetic fibers; and
 wherein the contacting at least a portion of the fiber web comprises contacting at least a portion of the first outer layer and/or at least a portion of the second outer layer with an aqueous natural binder to form the binder impregnated fiber web.

13. A multi-layer nonwoven fabric comprising a fiber web in an amount of about 98 wt. %, based on the total weight of the multi-layer nonwoven fabric; and a cured natural binder in an amount of about 2 wt. %, based on the total weight of the multi-layer nonwoven fabric; wherein the fiber web comprises a first outer layer, a second outer layer, and optionally one or more intermediate layers, wherein the one or more intermediate layers are disposed between the first outer layer and the second outer layer; wherein the first outer layer, the second outer layer, or both the first outer layer and the second outer layer comprise the cured natural binder; wherein each layer of the fiber web comprises natural fibers and synthetic fibers; wherein the natural fibers are present in the nonwoven fabric in an amount of about 80 wt. %, based on the total weight of the nonwoven fabric; wherein the synthetic fibers are present in the nonwoven fabric in an amount of about 18 wt. %, based on the total weight of the nonwoven fabric; wherein the cured natural binder comprises modified cellulose and a strengthening agent, wherein the cured natural binder is characterized by a weight ratio of strengthening agent to modified cellulose of from about 1:2 to about 1:1,000, wherein the modified cellulose comprises CMC and/or sodium CMC, wherein the strengthening agent comprises a crosslinking agent and a wet strength agent, wherein the crosslinking agent comprises a carboxylic acid having two or more carboxyl groups, wherein the wet strength agent comprises at least one reactive functional group selected from the group consisting of a halide group, a chloride group, a fluoride group, a hydroxyl group, and combinations thereof,
 wherein the natural fibers comprise cellulose fibers, wherein the synthetic fibers comprise biodegradable synthetic fibers, and wherein the nonwoven fabric is characterized by a degree of biodegradability of equal to or greater than about 99%, wherein the degree of biodegradability refers to aerobic biodegradability in soil as determined in accordance with ISO 17556:2003 E, and wherein the nonwoven fabric excludes latex and formaldehyde.

14. A single-layer nonwoven fabric comprising a fiber web in an amount of from about 85 wt. % to about 99.99 wt. %, based on the total weight of the single-layer nonwoven fabric; and a cured natural binder in an amount of from about 0.01 wt. % to about 15 wt. %, based on the total weight of the single-layer nonwoven fabric; wherein the fiber web comprises natural fibers; wherein the natural fibers are present in the single-layer nonwoven fabric in an amount of from about 85 wt. % to about 99.99 wt. %, based on the total weight of the single-layer nonwoven fabric; wherein the cured natural binder comprises modified cellulose and a strengthening agent in a weight ratio of strengthening agent to modified cellulose of from about 1:2 to about 1:1,000, wherein the modified cellulose comprises CMC and/or sodium CMC, wherein the strengthening agent comprises a crosslinking agent and a wet strength agent, wherein the crosslinking agent comprises a carboxylic acid having two or more carboxyl groups, wherein the wet strength agent comprises at least one reactive functional group selected from the group consisting of a halide group, a chloride group, a fluoride group, a hydroxyl group, and combinations thereof, wherein the natural fibers comprise cellulose fibers, wherein the synthetic fibers comprise biodegradable synthetic fibers, and wherein the nonwoven fabric is characterized by a degree of biodegradability of equal to or greater than about 99%, wherein the degree of biodegradability refers to aerobic biodegradability in soil as determined in accordance with ISO 17556:2003 E, and wherein the nonwoven fabric excludes latex and formaldehyde.

\* \* \* \* \*